United States Patent
Clary et al.

(10) Patent No.: US 11,382,756 B2
(45) Date of Patent: Jul. 12, 2022

(54) TOTAL KNEE IMPLANT PROSTHESIS ASSEMBLY AND METHOD

(71) Applicant: DePuy Ireland Unlimited Company, Ringaskiddy (IE)

(72) Inventors: Chadd W. Clary, Warsaw, IN (US); Paul J. Rullkoetter, Warsaw, IN (US); Mark A. Heldreth, Mentone, IN (US); Travis D. Bennett, Huntington, IN (US); Richard D. Komistek, Knoxville, TN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 85 days.

(21) Appl. No.: 16/591,828

(22) Filed: Oct. 3, 2019

(65) Prior Publication Data
US 2020/0030107 A1    Jan. 30, 2020

Related U.S. Application Data

(63) Continuation of application No. 16/246,910, filed on Jan. 14, 2019, now abandoned, which is a
(Continued)

(51) Int. Cl.
*A61F 2/38*      (2006.01)
*A61F 2/30*      (2006.01)

(52) U.S. Cl.
CPC .............. *A61F 2/3859* (2013.01); *A61F 2/38* (2013.01); *A61F 2/389* (2013.01); *A61F 2/3886* (2013.01);
(Continued)

(58) Field of Classification Search
CPC .......... A61F 2/38; A61F 2/3886; A61F 2/389; A61F 2002/30662
See application file for complete search history.

(56) References Cited

U.S. PATENT DOCUMENTS

| 3,765,033 A | 10/1973 | Goldberg et al. |
| 3,869,731 A | 3/1975 | Waugh et al. |

(Continued)

FOREIGN PATENT DOCUMENTS

| CN | 201438977 U | 4/2010 |
| CN | 101879099 A | 11/2010 |

(Continued)

OTHER PUBLICATIONS

Chinese Search Report for Chinese Application No. 201010173717.8, 2 Pages.
(Continued)

*Primary Examiner* — Brian A Dukert
(74) *Attorney, Agent, or Firm* — Barnes & Thornburg LLP

(57) ABSTRACT

A total knee implant prosthesis is disclosed. The total knee implant prosthesis includes a tibial component including a pair of bearing surfaces and a post positioned between the bearing surfaces, and a femoral component configured to rotate relative to the tibial component. The femoral component includes a pair of condyles sized and shaped to articulate on the bearing surfaces and a cam positioned between the pair of condyles. The cam engages the post at a first contact point when the femoral component is at 0 degrees of flexion and engages the post at a second contact point located lateral of the first contact point when the femoral component is at a first degree of flexion greater than 0 degrees. The cam is disengaged from the post when the femoral component is at a second degree of flexion greater than the first degree of flexion.

20 Claims, 15 Drawing Sheets

Related U.S. Application Data continuation of application No. 15/222,862, filed on Jul. 28, 2016, now Pat. No. 10,179,052.

(52) U.S. Cl.
CPC ............... *A61F 2002/30632* (2013.01); *A61F 2002/30662* (2013.01); *A61F 2310/00005* (2013.01); *A61F 2310/00023* (2013.01); *A61F 2310/00029* (2013.01); *A61F 2310/00059* (2013.01); *A61F 2310/00179* (2013.01)

(56) References Cited

U.S. PATENT DOCUMENTS

| | | | |
|---|---|---|---|
| 4,209,861 A | 7/1980 | Walker et al. |
| 4,215,439 A | 8/1980 | Gold et al. |
| 4,262,368 A | 4/1981 | Lacey |
| 4,340,978 A | 7/1982 | Buechel et al. |
| 4,470,158 A | 9/1984 | Pappas et al. |
| 4,888,021 A | 12/1989 | Forte et al. |
| 5,007,933 A | 4/1991 | Sidebotham et al. |
| 5,071,438 A | 12/1991 | Jones et al. |
| 5,133,758 A | 7/1992 | Hollister |
| 5,147,405 A | 9/1992 | Van Zile et al. |
| 5,219,362 A | 6/1993 | Tuke et al. |
| 5,326,361 A | 7/1994 | Hollister |
| 5,330,533 A | 7/1994 | Walker |
| 5,344,460 A | 9/1994 | Turanyi et al. |
| 5,358,527 A | 10/1994 | Forte |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,549,686 A | 8/1996 | Johnson et al. |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,658,342 A | 8/1997 | Draganich et al. |
| 5,681,354 A | 10/1997 | Eckhoff |
| 5,683,468 A | 11/1997 | Pappas |
| 5,702,458 A | 12/1997 | Burstein et al. |
| 5,702,466 A | 12/1997 | Pappas et al. |
| 5,755,801 A | 5/1998 | Walker et al. |
| 5,776,201 A | 7/1998 | Colleran et al. |
| 5,778,537 A | 7/1998 | Leini |
| 5,800,552 A | 9/1998 | Forte |
| 5,811,543 A | 9/1998 | Hao et al. |
| 5,824,100 A | 10/1998 | Kester et al. |
| 5,824,102 A | 10/1998 | Buscayret |
| 5,871,543 A | 2/1999 | Hofmann |
| 5,871,546 A | 2/1999 | Colleran et al. |
| 5,879,392 A | 3/1999 | Mcminn |
| 5,906,643 A | 5/1999 | Walker |
| 5,935,173 A | 8/1999 | Roger et al. |
| 5,964,808 A | 10/1999 | Blaha et al. |
| 5,997,577 A | 12/1999 | Herrington et al. |
| 6,004,351 A | 12/1999 | Tomita et al. |
| 6,013,103 A | 1/2000 | Kaufman et al. |
| 6,039,764 A | 3/2000 | Pottenger et al. |
| 6,056,779 A | 5/2000 | Noyer et al. |
| 6,080,195 A | 6/2000 | Colleran et al. |
| 6,123,729 A | 9/2000 | Insall et al. |
| 6,206,926 B1 | 3/2001 | Pappas |
| 6,264,697 B1 | 7/2001 | Walker |
| 6,299,646 B1 | 10/2001 | Chambat et al. |
| 6,325,828 B1 | 12/2001 | Dennis et al. |
| 6,344,059 B1 | 2/2002 | Krakovits et al. |
| 6,379,388 B1 | 4/2002 | Ensign et al. |
| 6,443,991 B1 | 9/2002 | Running |
| 6,475,241 B2 | 11/2002 | Pappas |
| 6,491,726 B2 | 12/2002 | Pappas |
| 6,540,787 B2 | 4/2003 | Biegun et al. |
| 6,558,426 B1 | 5/2003 | Masini |
| 6,582,469 B1 | 6/2003 | Tornier |
| 6,589,283 B1 | 7/2003 | Metzger et al. |
| 6,730,128 B2 | 5/2004 | Burstein |
| 6,764,516 B2 | 7/2004 | Pappas |
| 6,770,099 B2 | 8/2004 | Andriacchi et al. |
| 6,797,005 B2 | 9/2004 | Pappas |
| 6,846,329 B2 | 1/2005 | McMinn |
| 6,893,388 B2 | 5/2005 | Reising et al. |
| 6,893,467 B1 | 5/2005 | Bercovy |
| 6,916,340 B2 | 7/2005 | Metzger et al. |
| 6,926,738 B2 | 8/2005 | Wyss |
| 6,972,039 B2 | 12/2005 | Metzger et al. |
| 6,986,791 B1 | 1/2006 | Metzger |
| 7,025,788 B2 | 4/2006 | Metzger et al. |
| 7,066,963 B2 | 6/2006 | Naegerl |
| 7,081,137 B1 | 7/2006 | Servidio |
| 7,105,027 B2 | 9/2006 | Lipman et al. |
| 7,160,330 B2 | 1/2007 | Axelson, Jr. et al. |
| 7,261,740 B2 | 8/2007 | Tuttle et al. |
| 7,326,252 B2 | 2/2008 | Otto et al. |
| 7,422,605 B2 | 9/2008 | Burstein et al. |
| 7,572,292 B2 | 8/2009 | Crabtree et al. |
| 7,658,767 B2 | 2/2010 | Wyss |
| 7,678,152 B2 | 3/2010 | Suguro et al. |
| 7,842,093 B2 | 11/2010 | Peters et al. |
| 7,875,081 B2 | 1/2011 | Lipman et al. |
| 8,480,762 B2 | 7/2013 | Yoshimitsu |
| 8,628,579 B2 | 1/2014 | Ries et al. |
| 8,690,954 B2 | 4/2014 | Parisi et al. |
| 8,764,838 B2 | 7/2014 | Parisi et al. |
| 8,858,643 B2 | 10/2014 | Parisi et al. |
| 8,915,965 B2 * | 12/2014 | Komistek ............. A61F 2/3877 623/20.15 |
| 9,072,607 B2 | 7/2015 | Parisi et al. |
| 9,132,014 B2 | 9/2015 | Sanford et al. |
| 9,186,255 B2 | 11/2015 | Parisi et al. |
| 9,204,970 B2 | 12/2015 | Parisi et al. |
| 9,216,088 B2 | 12/2015 | Wasielewski |
| 9,295,558 B2 | 3/2016 | Parisi et al. |
| 9,320,616 B2 | 4/2016 | Samuelson et al. |
| 9,320,624 B2 | 4/2016 | Shin |
| 9,655,728 B2 | 5/2017 | Parisi et al. |
| 9,655,729 B2 | 5/2017 | Parisi et al. |
| 9,668,870 B2 | 6/2017 | Wasielewski |
| 9,788,954 B2 | 10/2017 | Parisi et al. |
| 9,925,050 B2 | 3/2018 | Parisi et al. |
| 9,962,264 B2 | 5/2018 | Komistek |
| 10,080,633 B2 | 9/2018 | Meerbeek et al. |
| 10,179,052 B2 | 1/2019 | Clary et al. |
| 10,201,429 B2 | 2/2019 | Enomoto et al. |
| 10,278,827 B2 | 5/2019 | Drury et al. |
| 10,478,307 B2 | 11/2019 | Wasielewski et al. |
| 10,898,337 B2 | 1/2021 | Parisi et al. |
| 2003/0009232 A1 | 1/2003 | Metzger et al. |
| 2004/0243244 A1 | 12/2004 | Otto et al. |
| 2004/0243245 A1 | 12/2004 | Plumet et al. |
| 2005/0096747 A1 * | 5/2005 | Tuttle ..................... A61F 2/389 623/20.32 |
| 2005/0143832 A1 | 6/2005 | Carson |
| 2005/0154472 A1 | 7/2005 | Afriat |
| 2005/0209701 A1 | 9/2005 | Suguro et al. |
| 2006/0015185 A1 | 1/2006 | Chambat et al. |
| 2006/0178749 A1 | 8/2006 | Pendleton et al. |
| 2007/0135926 A1 | 6/2007 | Walker |
| 2008/0021566 A1 | 1/2008 | Peters et al. |
| 2008/0119940 A1 | 5/2008 | Otto et al. |
| 2008/0243258 A1 | 10/2008 | Sancheti |
| 2008/0269596 A1 | 10/2008 | Revie et al. |
| 2009/0043396 A1 | 2/2009 | Komistek |
| 2009/0204221 A1 | 8/2009 | Walker |
| 2009/0306785 A1 | 12/2009 | Farrar et al. |
| 2009/0319047 A1 | 12/2009 | Walker |
| 2009/0326663 A1 | 12/2009 | Dun |
| 2010/0016977 A1 | 1/2010 | Masini |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2011/0118847 A1 | 5/2011 | Lipman et al. |
| 2014/0081412 A1 | 3/2014 | Metzger |

(56) References Cited

U.S. PATENT DOCUMENTS

| | | | |
|---|---|---|---|
| 2014/0257502 A1 | 9/2014 | Masini et al. | |
| 2014/0330388 A1 | 11/2014 | Mizuguchi et al. | |
| 2015/0088264 A1 | 3/2015 | Li et al. | |
| 2015/0134067 A1* | 5/2015 | Qu | A61F 2/3886 623/20.24 |
| 2015/0182344 A1 | 7/2015 | McKinnon et al. | |
| 2017/0266013 A1 | 9/2017 | Enomoto et al. | |
| 2019/0142595 A1 | 5/2019 | Clary et al. | |
| 2019/0209333 A1 | 7/2019 | Drury et al. | |
| 2019/0240032 A1 | 8/2019 | Wasielewski et al. | |
| 2020/0085583 A1 | 3/2020 | Hodge | |
| 2020/0100902 A1 | 4/2020 | Wasielewski et al. | |
| 2021/0068965 A1 | 3/2021 | Heldreth et al. | |
| 2021/0068966 A1 | 3/2021 | Wogoman et al. | |
| 2021/0068967 A1 | 3/2021 | Wogoman et al. | |
| 2021/0113340 A1 | 4/2021 | Parisi et al. | |
| 2021/0338440 A1 | 11/2021 | White et al. | |

FOREIGN PATENT DOCUMENTS

| | | |
|---|---|---|
| CN | 103126787 A | 6/2013 |
| CN | 103327937 A | 9/2013 |
| DE | 19529824 A1 | 2/1997 |
| EP | 636352 A2 | 2/1995 |
| EP | 732091 A2 | 9/1996 |
| EP | 1440675 A1 | 7/2004 |
| EP | 1591082 A2 | 11/2005 |
| EP | 2248488 A1 | 11/2010 |
| EP | 2254519 A1 | 12/2010 |
| EP | 2786727 A1 | 10/2014 |
| FR | 2417971 A1 | 9/1979 |
| FR | 2621243 A1 | 4/1989 |
| FR | 2787012 A1 | 6/2000 |
| FR | 2835178 A1 | 8/2003 |
| JP | 08500992 A | 2/1996 |
| JP | 2004167255 A | 6/2004 |
| WO | 0209624 A1 | 2/2002 |
| WO | 2004058108 A1 | 7/2004 |
| WO | 2005072657 A1 | 8/2005 |
| WO | 2007108804 A1 | 9/2007 |
| WO | 2007108933 A1 | 9/2007 |
| WO | 2007119173 A2 | 10/2007 |
| WO | 2013074142 A1 | 5/2013 |
| WO | 2013074143 A1 | 5/2013 |
| WO | 2013074144 A1 | 5/2013 |
| WO | 2013074145 A1 | 5/2013 |
| WO | 2014143538 A1 | 9/2014 |
| WO | 2015118517 A1 | 8/2015 |
| WO | 2016048800 A1 | 3/2016 |
| WO | 2020185908 A1 | 9/2020 |
| WO | 2020185912 A1 | 9/2020 |
| WO | 2021048236 A2 | 3/2021 |

OTHER PUBLICATIONS

European Search Report From Corresponding EPO App No. 06739287.8 dated Mar. 16, 2010, 3 Pages.

European Search Report in Corresponding EPO App No. 10162138.1 dated Aug. 30, 2010, 7 Pages.

European Search Report From Corresponding EPO App. No. 12164381.1-2310, dated May 18, 2012, 4 Pages.

European Search Report in Corresponding EPOapp. No. 12181217.6-2310, dated Jan. 15, 2013, 6 Pages.

European Search Report in Corresponding App. (I.E., 09164478.1-2310), dated Oct. 20, 2009, 6 Pages.

Australian Search Report for Corresponding App .. No. 2006340364, dated Dec. 11, 2009, 2 Pages.

Shaw, et al., "The Longitudinal Axis of the Knee & The Role of the Cruciate Ligaments in Controlling Transverse Rotation", J. Bone Joint Surg Am. 1974;56:1603-1609.

PCT Notification Concerning Transmittal of International Prel. Report for Corresponding International App. No. PCT/US2006/010431, dated Oct. 2, 2008, 6 Pages.

PCT Notification Concerning Transmittal of International Prel. Report for Corresponding International App. No. PCT/US2006/010431, dated Jun. 5, 2007, 8 Pages.

Andriacchi, T.P., "The Effect of Knee Kinematics, Gait and Wear On the Short and Long-Term Outcomes of Primary Knee Replacement," NIH Consensus Development Conference on Total Knee Replacement, pp. 61-64, Dec. 8-10, 2003, (4 Pgs).

Asano et al. "In Vivo Three-Dimensional Knee Kinematics Using a Biplanar Image-Matching Technique," Clin Orthop Rel Res, 388: 157-166, 2001 (10 Pgs).

Barnes, C.L., et al., Kneeling is Safe for Patients Implanted With Medial-Pivot Total Knee Arthroplasty Designs, Journal of Arthroplasty, vol. 00, No. 0 2010, 1-6, 6 Pgs.

Bertin et al., "In Vivo Determination of Posterior Femoral Rollback for Subjects Having a Nexgen Posterior Cruciate-Retaining Total Knff Arthroplasty," J Arthroplasty, vol. 17, No. 8, 2002, 9 Pages.

Blaha, et al., "Kinematics of the Human Knee Using an Open Chain Cadaver Model", Clinical Crthopaedics and Related Research, vol. 410 (2003); 25-34.

Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.

D'Lima et al., "Quadriceps Moment Arm and Quadriceps Forces After Total Knee Arthroplasty," Clin Orthop Rel Res 392:213-20, 2001.

Dennis, et al., "A Multicenter Analysis of Axial Femorotibial Rotation After Total Knee Arthroplasty", Clinical Orthopaedics 428(2004); 180-89.

Dennis, et al., "In Vivo Anteroposterior Femorotibial Translation of Total Knee Arthroplasty: A Mul ticenter Analysis," Clin Orthop Rel Res, 356: 47-57, 1998.

Dennis et al., "In Vivo Determination of Normal and Anterior Cruciate Ligament-Deficient Knee Kinematics," J Biomechanics, 38, 241-253, 2005, 13 Pgs.

Dennis et al "Multicenter Determination of in Vivo Kinematics After Total Knee Arthroplasty," Clin Orthop Rel Res., 416, 37-57, 21 Pgs.

Fan, Cheng-Yu, et al, Primitive Results After Medial-Pivot Knee Arthroplasties: A Minimum 5-Year Follow-Up Study, The Journal of Arthroplasty, vol. 25, No. 3 2010, 492-496, 5 Pgs.

Ferris, "Matching Observed Spiral Form Curves to Equations of Spirals in 2-0 Images,"The First Japanese-Australian Joint Seminar, 7 Pgs.

Freeman, Mar., et al, The Movement of the Normal Tibio-Femoral Joint, The Journal of Biomechanics 38 (2005) (2), pp. 197-208, 12 Pgs.

Fuller, et al.,"A Comparison of Lower-Extremity Skeletal Kinematics Measured Using Skin and Pin Mounted Markers", Human Movement Science 16 (1997) 219-242.

Goodfellow et al., "The Mechanics of the Knee and Prosthesis Design," The Journal of Bone and Joint Surgery, vol. 60-B, No. 3, 12 Pgs.

Hill, et al., "Tibiofemoral Movement 2: The Loaded and Unloaded Living Knee Studied by MRI" The Journal of Bone & Joint Surgery, vol. 82-B, No. 8 (Nov. 2000) 1196-1198.

P. Johal et al, "Tibio-Femoral Movement in the Living Knee. A Study of Weight Bearing and Non-Weight Bearing Knee Kinematics Using 'Interventional' MRI," Journal of Biomechanics, vol. 38, Issue 2, Feb. 2005, pp. 269-276 (8 Pgs).

Karachalios, et al., "A Mid-Term Clinical Outcome Study of the Advance Medial Pivot Knee Arthroplasty," www.sciencedirect.com, The Knee 16 (2009); 484-488.

Kessler et al., "Sagittal Curvature of Total Knee Replacements Predicts in Vivo Kinematics," Clinical Biomechanics 22(1): 52-58, 2007.

Komistek, et al., "In Vivo Fluoroscopic Analysis of the Normal Human Knee", Clinical Orthopaedics 410 (2003): 69-81.

Komistek, et al., "In Vivio Polyethylene Bearing Mobility is Maintained in Posterior Stabilized Total Knee Arthroplasty", Clinical Orthopaedics 428 (2004): 207-213.

(56) References Cited

OTHER PUBLICATIONS

Koo, et al., "The Knee Joint Center of Rotation is Predominantly on the Lateral Side During Normal Walking", Journal of Biomechanics, vol. 41 (2008); 1269-1273.

Li et al., "Anterior Cruciate Ligament Deficiency Alters the in Vivo Motion of the Tibiofemoral Cartilage Contact Points in Both Anteroposterior and Mediolateral Directions," JBJS-AM, vol. 88, No. 8, Aug. 2006, 9 Pgs.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756.

Moonot, et al., "Correlation Between the Oxford Knee and American Knee Society Scores at Mid-Term Folow-Up", The Journal of Knee Surgery, vol. 22, No. 3 (Jul. 2009), 226-230.

Murphy, Michael Charles, "Geometry and the Kinematics of the Normal Human Knee", Submitted to Massachusetts Institute of Technology (1990).

Nakagawa, et al., "Tibiofemoral Movement 3: Full Flexion in the Living Knee Studied by MRI", The Journal of Bone and Joint Surgery, vol. 82-B, No. 8 (Nov. 2000): 1199-1200.

"Nexgen Complete Knee Solution Cruciate Retaining Knee (CR)," Zimmer, Available at: http://zimmer.com.au/ctl?template=PC&op=global&action=&template=PC&id=356, downloaded on Feb. 18, 2009, (1 page).

Omori, et al., "The Effect of Geometry of the Tibial Polyethylene Insert on the Tibiofemoral Contact Kinematics in Advance Medical Pivot Total Knee Arthroplasty", The Journal of Orthopaedics Science (2009) 14: 754-760.

Ranawat, "Design May Be Counterproductive for Optimizing Flexion After TKR," Clin Orthop Rel Res 416: 174-6, 2003.

Ries, "Effect of ACL Sacrifice, Retention or Substitution on K After TKA," http://www.orthosupersite.comniew.asp.?RID=23134, Aug. 2007, 5 Pgs.

Saari et al., "The Effect of Tibial Insert Design on Rising From a Chair, Motion Analysis After Total Knee Replacement," Clin Biomech 19(9); 951-6, 2004.

"Scorpio Knee TS Single Axis Revision Knee System," Stryker Orthopaedics, http://www.stryker.com/stellenUgroups/public/documents/web prod/023609.pdf, (6 pgs).

Shakespeare, et al., "Flexion After Total Knee Replacement. A Comparison Between the Medial Pivot Knee and a Posterior Stabilised Implant," www.sciencedirect.com, The Knee 13 (2006): 371-372.

Suggs et al., "Three-Dimensional Tibiofemoral Articular Contact Kinematics of a Cruciate-Retaining Total Knee Arthroplasty," JBJS-AM, vol. 88-A, No. 2, 2006, 9 Pgs.

Vanguard Complete Knee System, Biomet, Available at http://www.biomet.com/patientsnanguard_complete.cfm, downloaded on Feb. 2009, 3 pgs.

Walker, et al., "Motion of a Mobile Bearing Knee Allowing Translation and Rotation", Journal of Arthroplasty 17(2002): 11-19.

Wang et al., "A Biomechanical Comparison Between the Single-Axis and Multi-Axis Total Knff Arthroplasty Systems for Stand-To-Sit Movement," Clin Biomech 20(4); 428-33, 2005.

Wang et al., "Biomechanical Differences Exhibited During Sit-to-Stand Between Total Knee Arthroplasty Designs of Varying Radii," J Arthroplasty 21 (8): 1193-1199, 2006.

Chinese First Office Action and Search Report, Chinese Application No. 20171062974 1X, dated Jul. 27, 2020, 8 pages.

Yoshiya et al., "In Vivo Kinematic Comparison of Posterior Cruciate-Retaining and Posterior-Stabilized Total Knee Arthroplasties Under Passive and Weight-Bearing Conditions," J Arthroplasty, vol. 20, No. 6, 2005, 7 Pgs.

Kurosawa, et al., "Geometry and Motion of the Knee for Implant and Orthotic Design". The Journal of Biomechanics vol. 18 No. 7(1985), pp. 487-499, 12 pages.

Japanese SR for Corresponding Patent Application No. 2009-501393, dated Oct. 26, 2010, 5 Pages.

EPO Search Report From Corresponding EPO Patent App No. 12164381.1-1654, dated Mar. 7, 2013, 3 Pages.

Uvehammer, et al., "In Vivo Kinematics of Total Knee Arthroplasty: Concave Versus Posterior-Stabilised Tibial Joint Surface," Journal of Bone & Joint Surgery, vol. 82-B, No. 1, May 2000, pp. 499-505.

Uvehammer et al., "In Vivo Kinematics of Total Knee Arthroplasty: Flat Compared With Concave Tibial Joint Surface," J Orthop Res 18(6):856-64, 2000.

European Search Report in EPO App. No. 09164478.1-2310 dated Apr. 28, 2010, 11 Pages.

European Search Report for European Patent Application No. 17178067.9-1664, dated Jan. 3, 2018.

Blaha, et al., "Advance Medial-Pivot and Stemmed Medial-Pivot Knee Systems," Wright Medical Technology, Inc. 2010.

"Persona The Personalized Knee Surgical Technique," Zimmer Biomet, 2018.

"Persona The Personalized Knee, Medial Congruent Bearing Design Rationale," Zimmer Biomet, 2017.

"eMP Evolution Medial-Pivot Knee System, The ACL-PCL Substituting Knee, Key Aspects," MicroPort Orthopedics, Inc., 2015.

"Evolution Medial-Pivot Knee System, Surgical Technique, Distal Cut First Instrumentation," MicroPort Orthopedics, Inc., 2014.

Zimmer NexGen Trabecular Metal Monoblock Tibial Components Surgical Technique Addendum, CR and LPS Articular Surface Geometry with a Trabecular Metal Base Plate, 2012, 7 pages, 97-7255-134-00 Rev. 1 3ML.

Zimmer Trabecular Metal Monoblock Tibial Components, Setting a New Gold Standard in Cementless TKA, 2007, 4 pages, 97-7255-133-00 5ML.

\* cited by examiner

TOTAL KNEE IMPLANT PROSTHESIS ASSEMBLY AND METHOD

This application is a continuation of U.S. patent application Ser. No. 16/246,910, filed Jan. 14, 2019, which is a continuation of U.S. patent application Ser. No. 15/222,862, now U.S. Pat. No. 10,179,052, filed Jul. 28, 2016. Both of the above-identified prior applications are expressly incorporated herein by reference.

TECHNICAL FIELD

The present disclosure relates to orthopedic knee prosthetics and, more specifically, to orthopedic knee prosthetics for use with total knee arthroplasty procedures.

BACKGROUND

The knee is the largest joint in the body. Normal knee function is required to perform most everyday activities. The knee is made up of the lower end of the femur, which rotates on the upper end of the tibia, and the patella, which slides in a groove on the end of the femur. Large ligaments attach to the femur and tibia to provide stability. The long thigh muscles give the knee strength and produces knee motion.

The joint surfaces where these three bones touch are covered with articular cartilage, a smooth substance that cushions the bones and enables them to move easily. The condition of this cartilage lining the knee joint is a key aspect of normal knee function and is important to the physician when evaluating a potential need for a knee joint replacement.

All remaining surfaces of the knee are covered by a thin, smooth tissue liner called the synovial membrane. This membrane releases a special fluid that lubricates the knee, reducing friction to nearly zero in a healthy knee.

Normally, all of these components work in harmony. But disease or injury can disrupt this harmony, resulting in pain, muscle weakness, and reduced function.

In addition to the smooth cartilage lining on the joint surfaces, there are two smooth discs of cartilage that cushion the space between the bone ends. The inner disc is called the medial meniscus, while the disc on the outer side of the knee joint is called the lateral meniscus. The role of the menisci is to increase the conformity of the joint between the femur and the tibia. The menisci also play an important function as joint shock absorbers by distributing weight-bearing forces, and in reducing friction between the joint segments.

There are also four major ligaments that play an important part in stability of the knee joint. The Medial Collateral Ligament (MCL) and the Lateral Collateral Ligament (LCL) are located on opposing sides on the outside of the joint. The Anterior Cruciate Ligament (ACL) and the Posterior Cruciate Ligament (PCL) are more centrally located ligaments within the joint. The ACL attaches to the knee end of the femur, at the back of the joint and passes down through the knee joint to the front of the flat upper surface of the Tibia. The ACL contacts the femur on the inner lateral condyle. When disrupted, this allows for laxity to occur on the lateral side of the knee. The ACL passes across the knee joint in a diagonal direction and with the PCL passing in the opposite direction, forms a cross shape, hence the name cruciate ligaments.

Total knee replacement (TKR), also referred to as total knee arthroplasty (TKA), is a surgical procedure where worn, diseased, or damaged surfaces of a knee joint are removed and replaced with artificial surfaces. Materials used for resurfacing of the joint are not only strong and durable but also optimal for joint function as they produce as little friction as possible.

The "artificial joint or prosthesis" generally has three components: (1) a distal femoral component usually made of a biocompatible material such as metal alloys of cobalt-chrome or titanium; (2) a proximal tibial component also made of cobalt chrome or titanium alloy; and a bearing component disposed there between usually formed of a plastic material like polyethylene.

In total knee arthroplasty (TKA) there are three main types of implants: The first main type is the posterior cruciate retaining (PCR) total knee arthroplasty, where the surgeon retains the posterior cruciate ligament and sacrifices the anterior cruciate ligament. The second main type is the posterior stabilizing (PS) total knee arthroplasty, where the surgeon sacrifices both the anterior cruciate ligament (ACL) and the posterior cruciate ligament (PCL). With a PS TKA posterior stabilization is introduced into the TKA by using a cam/post mechanism. The third main type is the posterior cruciate sacrificing (PCS) TKA where the surgeon sacrifices both the ACL and the PCL, but does not use a cam/post mechanism for posterior stabilization. Rather, this TKA type uses constraint in the polyethylene to stabilize the antero-posterior movement.

Any of the above three main types of TKA implant can have a fixed bearing (FB) design or a mobile bearing (MB) design. With the fixed bearing design, the polyethylene insert is either compression molded or fixed in the tibial tray using a locking mechanism. In a mobile bearing design, the polyethylene insert is free to either rotate, translate or both rotate and translate.

While knee arthroplasty is known as one of the most consistently successful surgeries offered, there is room for improvement. For example, the ACL is sacrificed during the installation of a total knee arthroplasty system, and doing so can have a negative clinical impact for some patients.

The role of the ACL is to pull the femur in the anterior direction at terminal extension and at full extension. The ACL, attached to the lateral condyle of the femur also works as a tether and keeps the lateral condyle in contact with the lateral meniscus. The PCL pulls the femur in the posterior direction with increasing flexion. The PCL also acts as a tether on the medical condyle of the femur, keeping the medial condyle in contact with the medial meniscus. Together these two ligaments are vitally important to the stability of the knee joint, especially in contact sports and those that involve fast changes in direction and twisting and pivoting movements. Therefore, a torn or absent ACL has serious implications for the stability and function for the knee joint. In other orthopedic fields, surgeons usually recommend ACL replacement surgery for a torn ACL because without the ACL, the femorotibial joint becomes unstable. It is assumed that this instability leads to meniscus and cartilage damage. Unfortunately, the ACL is sacrificed in TKA.

Attempts have been made to design a TKA that retains the ACL, but these procedures are often very difficult to perform and the function of the ACL is often compromised. Fluoroscopic studies have been conducted on previous ACL retaining TKA designs and they have reported that these patients have difficulty achieving full extension and often experience a very tight knee at 90 degrees of knee flexion, under weight-bearing conditions. This is probably due to the knee joint becoming overly constrained due to the retention of the cruciate ligaments, but the patient's geometrical condylar shapes being altered. Sacrificing the ACL contributes to laxity in the joint that allows the femur freedom of motion due to the changes in their condylar shapes.

Known TKA implants, such as PS and PCR TKA, provide for posterior stabilization, but not anterior stabilization. What is needed, therefore, is a TKA implant that provides for anterior stabilization in the absence of a surgically removed ACL while also accommodating a retained PCL.

Introduction

According to one aspect of the disclosure, a total knee implant prosthesis comprises a femoral component including a pair of condyles and a cam positioned between the pair of condyles. The cam has a convex curved surface including a center point that is laterally offset from a center line of the femoral component when the femoral component is viewed in a first plane. It should be appreciated that the first plane may correspond to a traverse plane of a patient's body. The total knee implant prosthesis further comprises a tibial component including a medial bearing surface, a lateral bearing surface, and a post positioned between the medial bearing surface and the lateral bearing surface. The post has a curved surface that is angled to face toward the medial bearing surface and away from the lateral bearing surface when the tibial component is viewed in the first plane. The femoral component is configured to rotate relative to the tibial component between a full extension position and a full flexion position, and the cam and the post are sized, shaped, and positioned so that the cam engages the post at a contact point on the curved surface of the post when the femoral component is in the full extension position. When the femoral component is rotated from the full extension position toward the full flexion position, the cam and the post are sized, shaped, and positioned so that the contact point moves laterally along the curved surface of the post. The cam and the post are also sized, shaped, and positioned so that the cam is disengaged from the post when the femoral component is in the full flexion position.

In some embodiments, the tibial component may have a medial-lateral center line when the tibial component is viewed in the first plane, and the post may have a medial-lateral center line that is laterally offset from the medial-lateral center line of the tibial component when the tibial component is viewed in the first plane.

In some embodiments, the curved surface of the post may define an arced line having a center point that lies on the medial-lateral center line of the post when the tibial component is viewed in the first plane. In some embodiments, the arced line is convex. In some embodiments, the arced line may have a radius extending from an origin that is offset in a lateral direction from the medial-lateral center line of the post. The radius may be offset by a distance equal to less than 6 mm. In other embodiments, the distance may be less than or equal to 12 mm.

Additionally, in some embodiments, the medial bearing surface may include a distal-most point, and a distance may be defined in an anterior-posterior direction between the center point and the distal-most point of the medial bearing surface. The distance may be greater than 0 mm and less than or equal to about 10 mm. In other embodiments, the distance may be greater than 0 mm and less than or equal to about 15 mm.

In some embodiments, the medial-lateral center line of the post may be offset in a lateral direction from the medial-lateral center line of the tibial component by a distance that is equal to less than 6 mm. In other embodiments, the distance may be less than or equal to 12 mm.

In some embodiments, when the tibial component is viewed in a second plane extending orthogonal to the first plane, the curved surface of the post may define a concave curved line. It should be appreciated that the second plane may correspond to the sagittal plane of the patient's body. In some embodiments, the concave curved line may be defined by a radius that is in a range of 3 mm to 25 mm. In other embodiments, the distance may be in a range of 3 mm to 30 mm. In some embodiments, when the tibial component is viewed in the first plane, the curved surface may define a convex curved line.

In some embodiments, the medial bearing surface and the lateral bearing surface may be asymmetrical. Additionally, in some embodiments, the lateral bearing surface may be flatter than the medial bearing surface.

According to another aspect, a total knee implant prosthesis comprises a tibial component including a pair of bearing surfaces and a post positioned between the bearing surfaces, and a femoral component configured to rotate relative to the tibial component. The femoral component includes a pair of condyles sized and shaped to articulate on the bearing surfaces and an anterior cam positioned between the pair of condyles. The cam engages the post at a first contact point when the femoral component is at 0 degrees of flexion, and the cam engages the post at a second contact point located lateral of the first contact point when the femoral component is at a first degree of flexion greater than 0 degrees. Additionally, the cam is disengaged from the post when the femoral component is at a second degree of flexion greater than the first degree of flexion.

In some embodiments, the post may have a medial-lateral center line when the tibial component is viewed in a first plane, the first contact point may be located medial of the medial-lateral center line, and the second contact point may be located lateral of the medial-lateral center line.

In some embodiments, the tibial component may have a medial-lateral center line when the tibial component is viewed in the first plane. The medial-lateral center line of the post may be laterally offset from the medial-lateral center line of the tibial component when the tibial component is viewed in the first plane.

Additionally, in some embodiments, the cam may include a posterior surface configured to engage an anterior surface of the post at the first contact point and the second contact point. The posterior surface of the cam may define a convex curved line when the femoral component is viewed in a first plane, and the anterior surface of the post may define a convex curved line when the femoral component is viewed in the first plane.

In some embodiments, the anterior surface of the post may define a concave curved line when the tibial component is viewed in a second plane positioned orthogonal to the first plane. In some embodiments, the convex curved line that is defined by the cam may have a center point that is laterally offset from a center line of the femoral component when the femoral component is viewed in a first plane.

In some embodiments, the cam may be configured to engage an anterior surface of the post that is angled to face toward a medial bearing surface of the pair of bearing surfaces and away from a lateral bearing surface of the pair of bearing surfaces.

BRIEF DESCRIPTION OF THE DRAWINGS

The detailed description particularly refers to the following figures, in which.

DETAILED DESCRIPTION OF THE DRAWINGS

Figure 1:
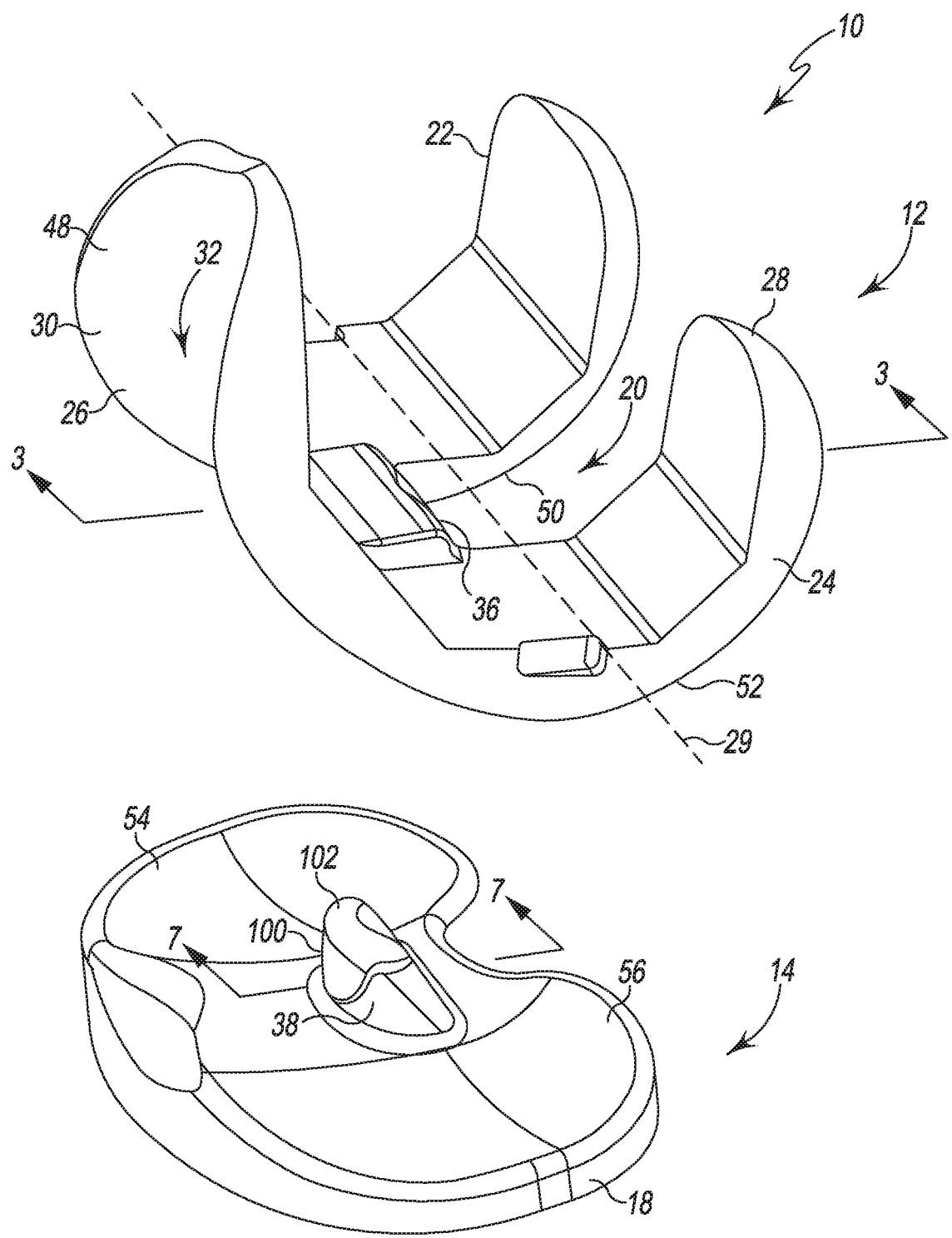
FIG. 1 is an exploded perspective view of an exemplary embodiment of a replacement knee prosthesis providing anterior stabilization.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referring now to FIG. 1, an exemplary embodiment of an orthopedic knee implant 10 for use with total arthroplasty procedures is shown. The implant 10 includes a femoral component 12 and a tibial component 14 that is configured to permit the femoral component 12 to articulate over a range of flexion. In this exemplary embodiment, the tibial component 14 comprises a tibial tray insert 18, which is configured to be attached to, for example, a tibial tray (not shown) adapted to be secured to the proximal end of a tibia. Such trays may include stems configured to be received within the intramedullary canal of the tibia. It should be appreciated that the tray may provide either a fixed bearing interface to lock the orientation of the tibial tray insert 18 with the tibial tray or a mobile bearing interface that allows the tibial tray insert 18 to move independent of the tibial tray. Additionally, in other embodiments, the tibial tray and the tibial tray insert may be combined into a single, monolithic component.

The femoral component 12 is illustratively formed from a metallic material such as cobalt-chromium or titanium, but may be formed from other materials, such as a ceramic material, a polymer material, a bio-engineered material, or the like, in other embodiments. The tibial tray insert 18 is illustratively formed from a polymer material such as an ultra-high molecular weight polyethylene (UHMWPE), but may be formed from other materials, such as a ceramic material, a metallic material, a bio-engineered material, or the like, in other embodiments.

As shown in FIG. 1, the femoral component 12 is illustratively a posterior cruciate retaining orthopedic femoral component that includes a posterior discontinuity or gap 20 between lateral and medial condyles 22, 24 to allow the femoral component to rotate between maximum extension and maximum flexion without impinging the posterior cruciate ligament (PCL), which is retained during the total arthroplasty procedure. In contrast, the anterior cruciate ligament (ACL) is sacrificed or removed during a total arthroplasty procedure. Those skilled in the art are familiar with the posterior constraint resulting from retention of the posterior cruciate ligament, whereas those skilled in the art are also familiar with the absence of anterior constraint resulting from the absence of the anterior cruciate ligament.

The exemplary femoral component 12 includes a pair of condyles 22, 24, each of which has an arcuate shape in order to allow for smooth rotation of the femur with respect to the tibia. In general, the femoral component includes an anterior portion 26 and a posterior portion 28 that are shown by the dotted line imaginary boundary line 29 in FIG. 1. The anterior portion 26 includes a front exterior face 30 having a depression 32 adapted to receive at least a portion of a patella component. The depression 32 marks the beginning of individual condyle 22, 24 formation. From the top or superior-most portion of the front face 30 downward, following the contours of the front face, the curved nature of begins to take shape and transition into individual condyles 22, 24. As the shape of the condyles 22, 24 becomes more pronounced, the condyles separate from one another, which is marked by an arcuate bridge 34 (see FIG. 3) formed at the distal end of the depression 32. In the illustrative embodiment, the arcuate bridge 34 defines the anterior end of the gap 20 between the condyles 22, 24. The femoral component 12 also includes an anterior cam 36 that is positioned posterior of, and superior to, the arcuate bridge 34. As described in greater detail below, the anterior cam 36 is configured to engage a post 38 of the tibial component 14.

The front exterior face 30 of the femoral component 12 includes an articulation surface 48 that is configured to engage a corresponding surface of a patella component. The articulation surface 48 defines the depression 32 and includes the arcuate bridge 34. At the arcuate bridge, the articulation surface 48 separates into a medial articulation surface 50 of the medial condyle 22 and a lateral articulation surface 52 of the lateral condyle 24. The surfaces 50, 52 are configured to engage with and articulate on corresponding bearing surfaces 54, 56, respectively, of the tibial component 14. The articulation surfaces 50, 52 of the condyles 22, 24 flatten out and do not exhibit a uniform arcuate shape from anterior to posterior. Additionally, as illustrated in FIG. 1, the medial condyle 22 has a maximum medial-lateral width that is larger than the maximum medial-lateral width of the lateral condyle 24. However, in the illustrative embodiment, the gap 20 has a substantially uniform width, resulting in the inner shape and contour of the condyles being substantially the same.

Figure 3:
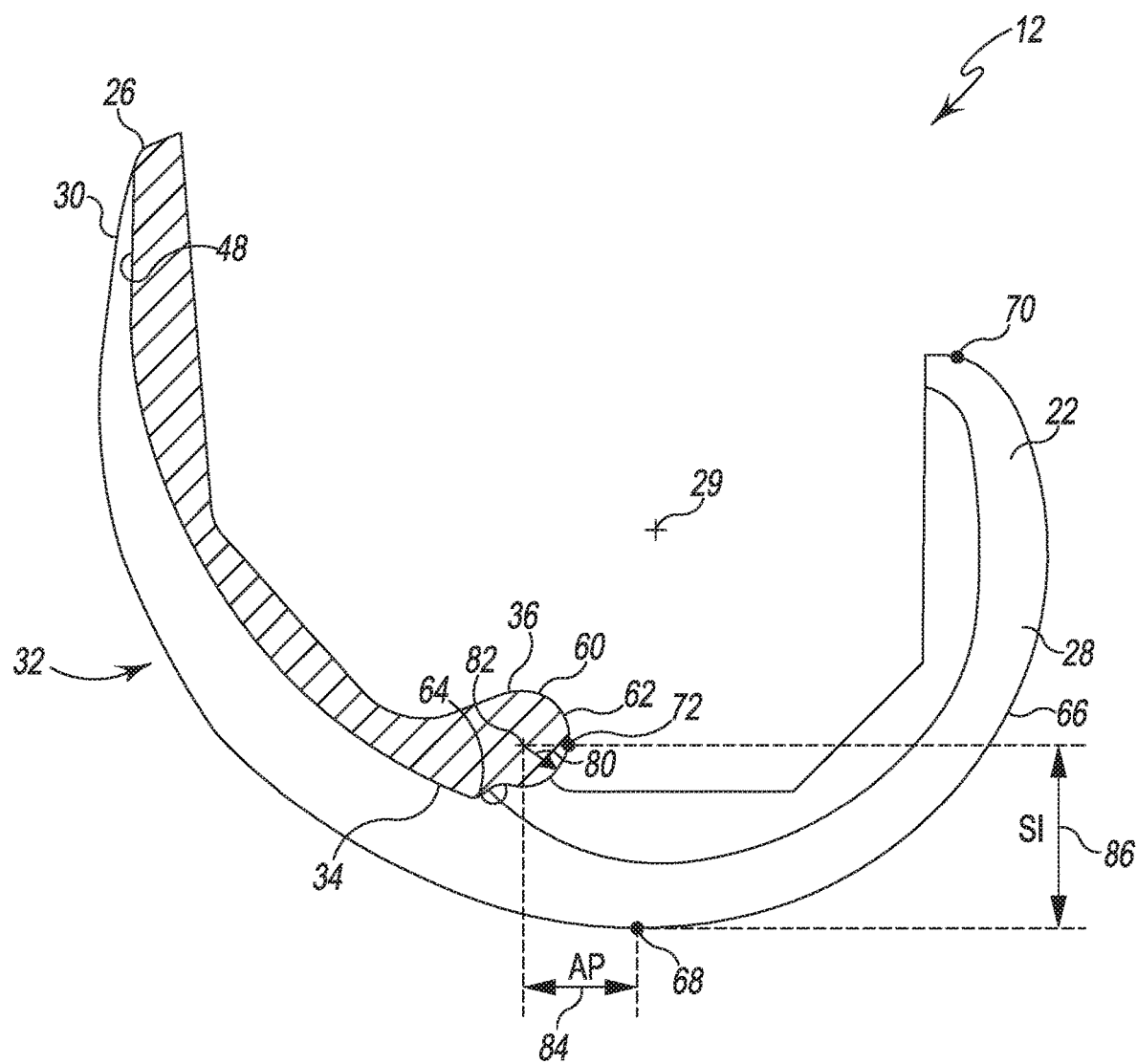
FIG. 3 is a cross-sectional elevation view taken along the line 3-3 in FIG. 1 illustrating the femoral component of the replacement knee prosthesis of FIGS. 1-2.
Figure 4:
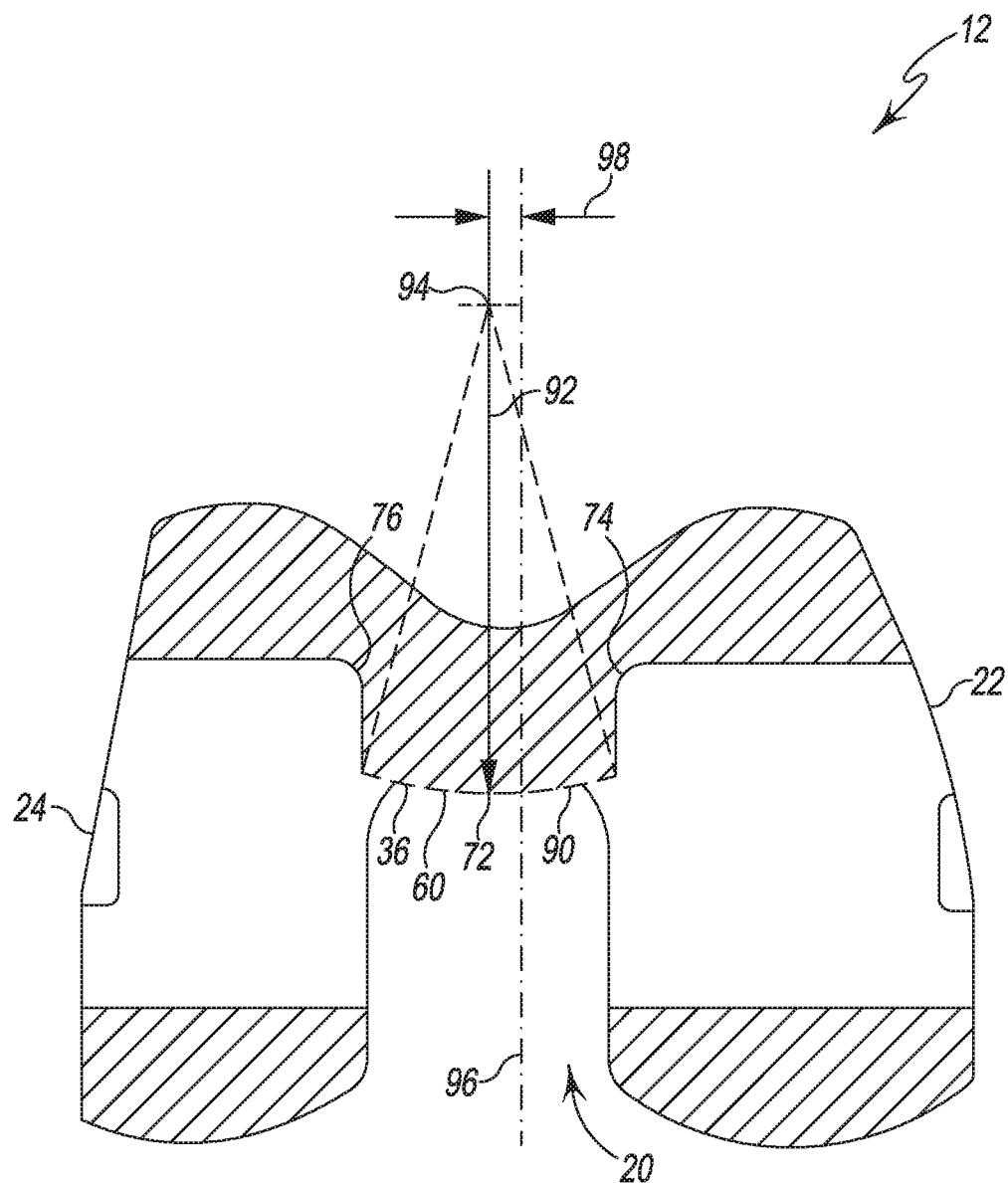
FIG. 4 is a cross-sectional plan view taken along the line 4-4 in FIG. 2 illustrating the femoral component of the replacement knee prosthesis of FIG. 1 in a plane extending perpendicular to the plane shown in FIG. 3.

As shown in FIGS. 3-4, the anterior cam 36 of the femoral component 12 has a posterior surface 60 that is arcuate or rounded when the femoral component is viewed in the plane shown in FIG. 3, which may correspond to the sagittal plane of the patient's body with the femoral component 12 is implanted therein. In the illustrative embodiment, the surface 60 defines a convex curved line 62 when viewed in the plane of FIG. 3, but it should be appreciated that in other embodiments the camming surface may define a concave curved line. In still other embodiments, the camming surface may define a substantially straight line for a substantially flat or planar cam. As described above, the anterior cam 36 is positioned posterior of, and superior to, the arcuate bridge 34. As shown in FIG. 3, the anterior cam 36 is connected to the arcuate bridge 34 via a connecting surface 64 extending superiorly from the arcuate bridge 34 between the condyles 22, 24.

When viewed in the plane of FIG. 3, the medial articulation surface 50 of the femoral component 12 defines an arcuate line 66 extending from a distal-most point 68 of the medial articulation surface 50 to a superior-most point 70. In the illustrative embodiment, the distal-most point 68 of the medial articulation surface 50 lies in a plane with the boundary line 29 that marks the division of the femoral component 12 into the anterior portion 26 and the posterior portion 28. As shown in FIG. 3, the posterior-most point 72 of the medial surface 50 is positioned anterior of the distal-most point 68 of the medial articulation surface 50. In that way, the anterior cam 36 is positioned entirely in the anterior portion 26 of the femoral component 12.

As shown in FIG. 3, the curved line 62 (and hence the surface 60 in the plane of FIG. 3) has a radius 80 that extends from an origin 82 positioned anterior of, and superior to, the distal-most point 68 of the medial articulation surface 50. A pair of distances 84, 86 are defined between the point 68 and the origin 82 in the anterior-posterior direction and superior-inferior direction, respectively. In the illustrative embodiment, the anterior-posterior distance 84 is equal to about 6.25 mm. A person of ordinary skill would understand that the term "about" as used herein accounts for typical manufacturing or measurement tolerances present in the manufacture or use of prosthetic components. Exemplary manufacturing tolerances include 0.1 millimeters. In other embodiments, the anterior-posterior distance 84 between the origin 82 and the distal-most point 68 of the medial surface 50 may be in a range of about 0 mm to about 12 mm.

The superior-inferior distance 86 between the distal-most point 68 and the origin 82 (and also the posterior-most point 72 of the cam 36) is equal to about 12.25 mm in the illustrative embodiment. In other embodiments, the distance 86 may be in a range of about 5 mm to about 20 mm. The radius 80 of the surface 60 is illustratively equal to about 3 mm, but, in other embodiments, the radius 80 may be in a range of about 1 mm to about 6 mm. In still other embodiments, the radius 80 may be greater than 6 mm. It should be appreciated that in other embodiments the radius 80 and the distances 84, 86 may be greater or less than these ranges depending on the physical requirements of a particular patient.

Referring now to FIG. 4, the surface 60 of the cam 36 is illustratively shown as arcuate or rounded when viewed in a plane extending perpendicular to the plane shown in FIG. 3, which may correspond to the transverse plane of the patient's body with the femoral component 12 is implanted therein. In the illustrative embodiment, the surface 60 defines a convex curved line 90 that extends from a medial end 74 to a lateral end 76 when viewed in the plane shown in FIG. 4. It should be appreciated that in other embodiments the surface may define a concave curved line in the transverse plane. In still other embodiments, the posterior surface may define a substantially straight line for a substantially flat or planar cam. As described above, the cam 36 is convex and curved when viewed in either the sagittal or the transverse plane. It should be appreciated that in other embodiments the cam 36 may include any combination of convex, concave and/or flat surfaces in those planes. For example, in some embodiments, the cam 36 may be convex when viewed in the sagittal plane and concave when viewed in the transverse plane.

As shown in FIG. 4, the curved line 90 (and hence the posterior surface 60 in the plane shown in FIG. 4) has a radius 92 that extends from an origin 94. The radius 92 of the surface 60 is equal to about 33 mm in the illustrative embodiment. In other embodiments, the radius 92 may be in a range of about 10 mm to about 33 mm. In still other embodiments, the radius 92 may be greater than 33 mm.

As shown in FIG. 4, the femoral component 12 has a medial-lateral center line 96 that extends in the anterior-posterior direction. In the illustrative embodiment, the origin 94 is offset from the center line 96 in a lateral direction by a medial-lateral distance 98. The distance 98 is equal to about 3 mm. In other embodiments, the distance 98 between the origin 94 and the central axis 682 may be in a range of about 0 mm to about 6 mm. In still other embodiments, the distance 688 may be greater than 6 mm.

In the illustrative embodiment, the posterior-most point 72 is the medial-lateral mid-point of the surface 60 of the cam 36. As shown in FIG. 4, the posterior-most point 72 is offset by the same distance 98 from the center line 96. As a result, the surface 60 (and hence the cam 36) is offset laterally from the center line 96. It should be appreciated that in other embodiments the posterior-most point of the camming surface may be offset from the center line 96 less than or greater than the origin 94. For example, the origin 94 may be offset from the center line 96 while the posterior-most point of the camming surface intersects with the center line 96. It should also be appreciated that in other embodiments the radius 92 and the distance 98 may be greater or less than these ranges depending on the physical requirements of a particular patient.

In the illustrative embodiment, the center line of the gap 20 is also offset by the same distance 98 from the center line 96 of the femoral component 12. In that way, the gap 20 is laterally offset in the femoral component 12. It should be appreciated that in other embodiments the distance 98 may be greater or less than these ranges depending on the physical requirements of a particular patient. In other embodiments, the center line of the gap 20 offset from the center line by a different distance than the other structures of the femoral component 12. In still other embodiments, the center line of the gap 20 may not be offset at all.

Returning to FIG. 1, the implant 10 also includes a tibial tray insert 18. As described above, the tibial tray insert 18 includes bearing surfaces 54, 56 that are adapted to receive and engage the condyles 22, 24 of the femoral component 12. The two bearing surfaces 54, 56 are partially separated from one another by a post 38 upstanding from the tibial tray insert 18. In this exemplary embodiment, the post 38 is integrally formed with the tibial tray insert 18. However, it should be appreciated that the post 38 may be separable from the tibial tray insert 18 and its location is independent of the location/movement of the tibial tray insert.

Figure 2:
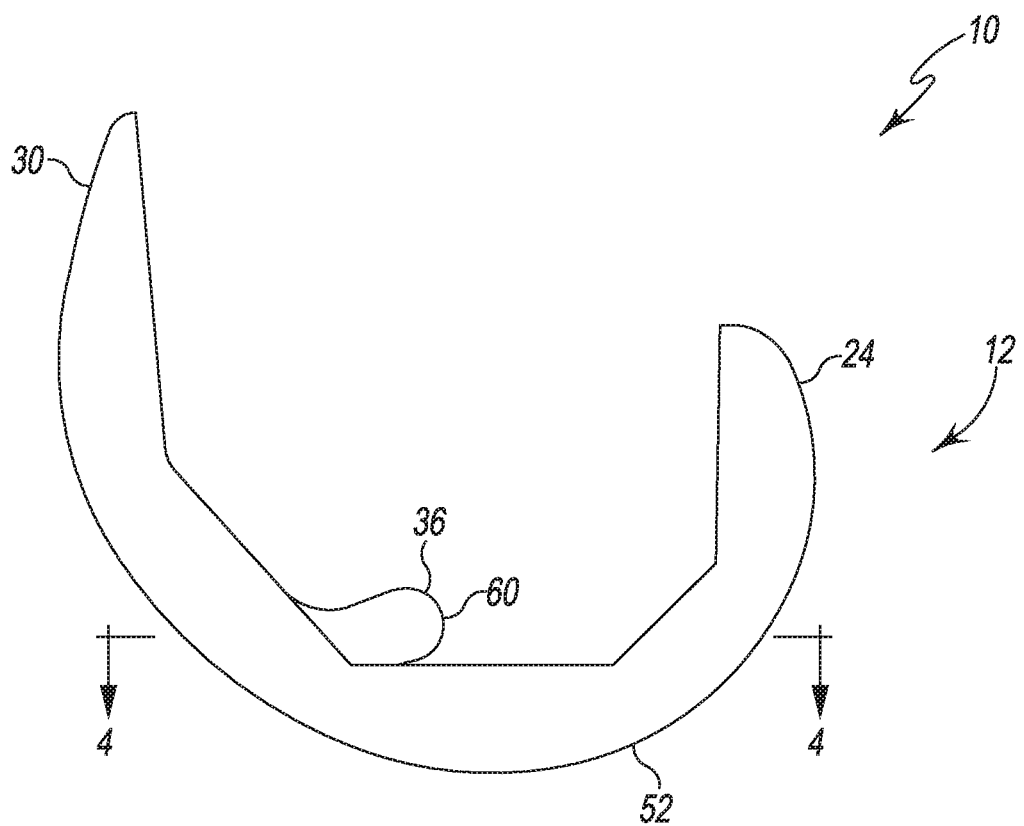
FIG. 2 is an exploded elevation view illustrating the replacement knee prosthesis of FIG. 1.
Figure 2:
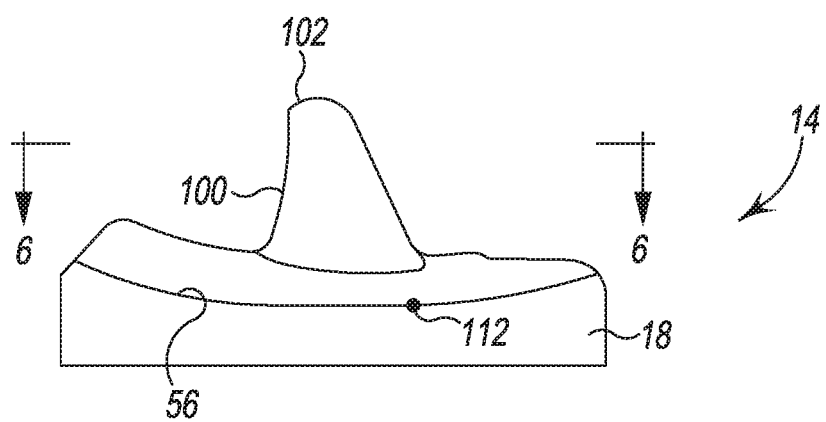

The post 38 has an anterior surface or wall 100 that is configured to engage the posterior surface 60 of the cam 36 of the femoral component 12 when the implant 10 (and hence the knee) is at full extension and over part of flexion. As shown in FIG. 2, the post 38 also includes a curved anterior section 102 that is sized to ensure the cam 36 properly disengages from the post 38. It should be appreciated that the post 38 may include other structure that is sized and shaped to ensure the cam 36 properly disengages from the post 38.

The bearing surfaces 54, 56 are illustratively concave surfaces. Additionally, as shown in FIG. 2, the surfaces 54, 56 are asymmetrical and share a common posterior geometry before diverging as they progress anteriorly, with the lateral surface 56 having a flatter anterior section than the medial surface 54. In the illustrative embodiment, the medial surface 54 has a distal-most point 112 that is proximate to where the geometries of the surfaces 54, 56 begin to diverge. It should be appreciated that in other embodiments the surfaces 54, 56 may be symmetrical and have substantially identical geometries.

Figure 5:
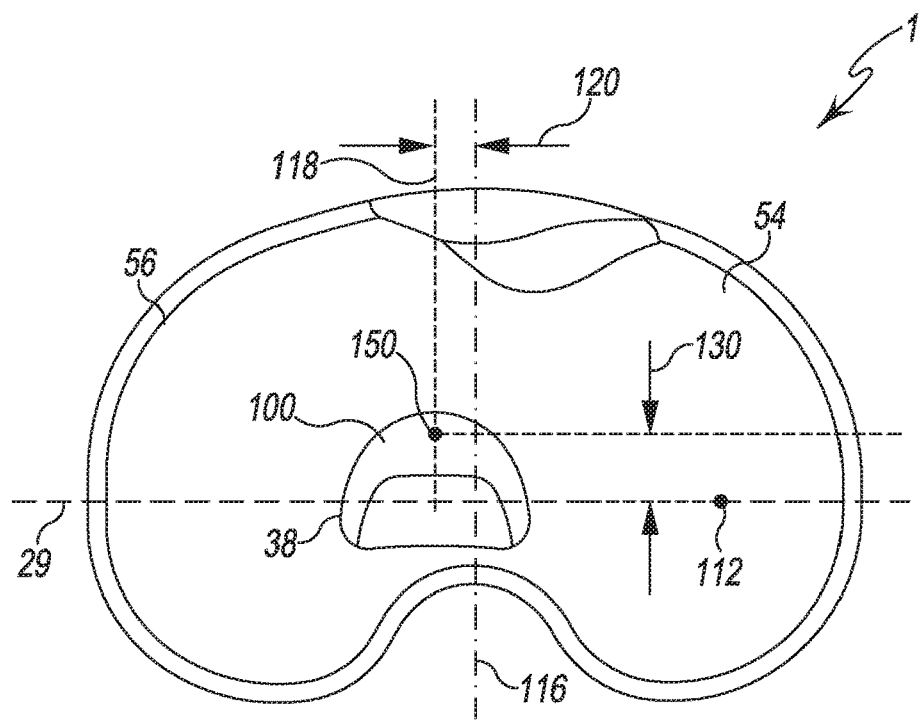
FIG. 5 is a plan view illustrating the tibial component of the replacement knee prosthesis of FIG. 1.

Referring now to FIG. 5, a medial-lateral center line 116 that extends in the anterior-posterior direction indicates the medial-lateral mid-line of the tibial insert 18. Another medial-lateral center line 118 that extends in the anterior-posterior direction indicates the medial-lateral mid-line of the post 38. In the illustrative embodiment, the post center line 118 is offset from and extends parallel to the center line 116 of the insert 18. A distance 120 is defined between lines 116, 118; in the illustrative embodiment, the distance 120 is equal to about 3 mm such that the post line 118 (and hence the post 38 itself) is offset in a lateral direction from the central line 116. In other embodiments, the distance 120 may be in a range of about 0 mm to about 6 mm. In still other embodiments, the distance 120 may be greater than 6 mm.

As shown in FIG. 5, the anterior wall 100 is positioned anterior of the distal-most point 112 of the medial bearing surface 54, which lies in a plane with the boundary line 29. In that way, the anterior wall 100 is positioned entirely in the anterior portion of the tibial insert 18. In the illustrative embodiment, a distance 130 extending in an anterior-posterior direction is defined between the distal-most point 112 and the anterior wall 100. The distance 130 is illustratively equal to about 6 mm; in other embodiments, the distance 130 may be in a range of 0 mm to 10 mm. In still other embodiments, the distance may be greater than 10 mm.

Figure 6:
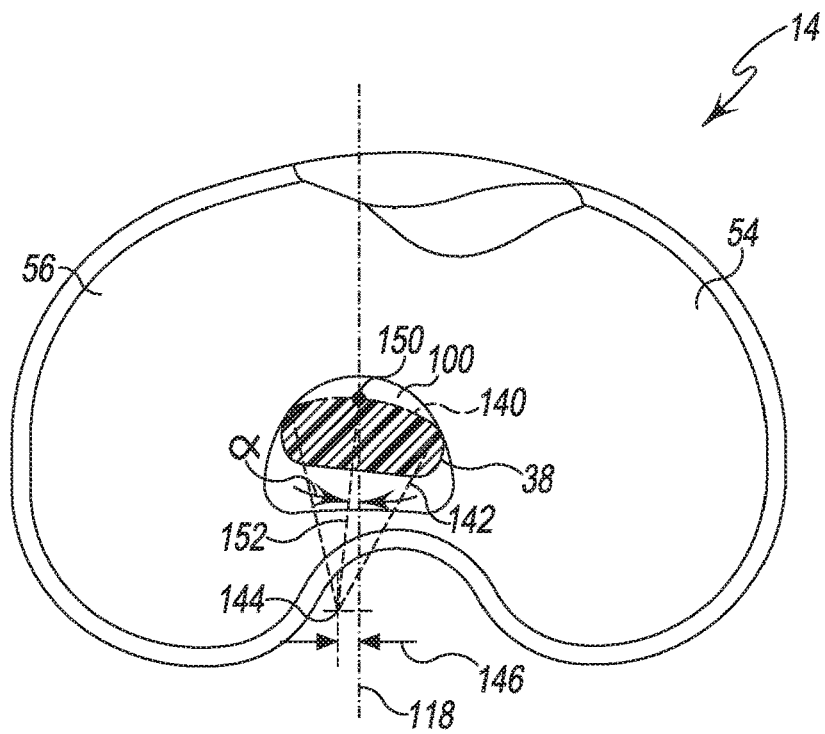
FIG. 6 is a cross-sectional plan view taken along the line 6-6 in FIG. 2 illustrating the tibial component of the replacement knee prosthesis of FIG. 1.

In the illustrative embodiment, the anterior wall 100 of the post 38 is arcuate or rounded when the post 38 is viewed in a transverse plane. As shown in FIG. 6, the anterior wall 100 defines a convex curved or arced line 140 when viewed in the transverse plane, but it should be appreciated that in other embodiments the anterior wall may define a concave arced line. In still other embodiments, the camming surface may define a substantially straight line for a substantially flat or planar surface.

The arced line 140 (and hence the anterior wall 100 in the transverse plane) has a radius 142 that extends from an origin 144. As shown in FIG. 6, a distance 146 extending in a medial-lateral direction is defined between the origin 144 and the post center line 118. In the illustrative embodiment, the distance 146 is equal to about 1.2 mm such that the origin 144 is offset from the post center line 118 in a lateral direction. In other embodiments, the distance 146 may be equal to about 0 mm to about 6 mm. In still other embodiments, the distance may be greater than 6 mm.

Due to the combination of the distances 120, 146, the origin 144 is offset laterally from the central line 116 of the tibial insert 18 by about 4.2 mm. In other embodiments, the origin 144 may be offset in a range of about 0 mm to about 12 mm.

As shown in FIG. 6, the radius 142 of the anterior wall 100 is illustratively equal to about 15 mm, but, in other embodiments, the radius 142 may be in a range of about 10 mm to about 15 mm. In still other embodiments, the radius may be greater than 15 mm. It should be appreciated that in other embodiments the radius 142 and the distances 120, 130, and 146 may be greater or less than these ranges depending on the physical requirements of a particular patient.

In the illustrative embodiment, the anterior wall 100 of the post 38 is angled toward the medial bearing surface 54. As shown in FIG. 6, the arced line 140 defined by the anterior wall 100 intersects the post center line 118 at a point 150, and a straight imaginary line 152 extends from the origin 144 through the point 150 such that an angle α is defined between the imaginary line 152 and the post center line 118. In the illustrative embodiment, the angle α is equal to about 4.6 degrees, indicating the amount that the anterior wall 100 is angled toward the medial bearing surface 54.

Figure 7:
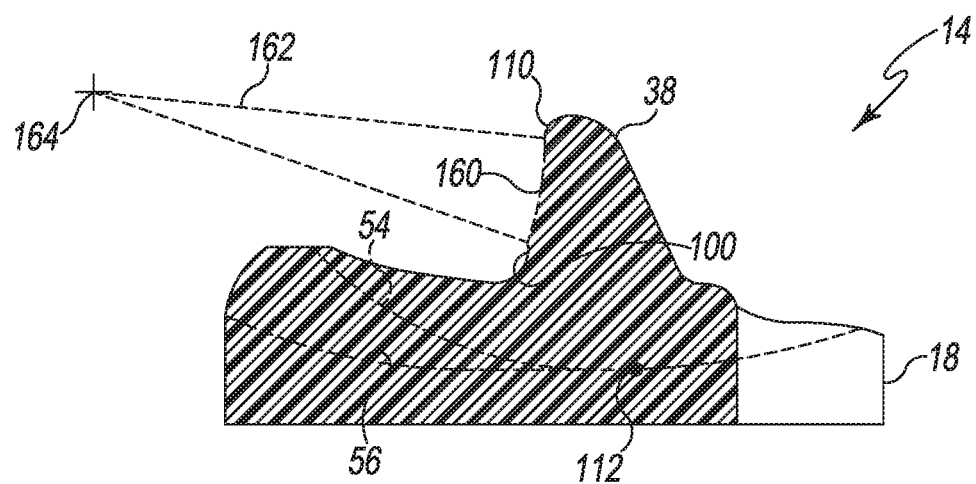
FIG. 7 is an elevation view taken along the line 7-7 in FIG. 1 illustrating the tibial component of the replacement knee prosthesis of FIGS. 1-2 in a plane extending perpendicular to the plane shown in FIG. 5.
Figure 8:
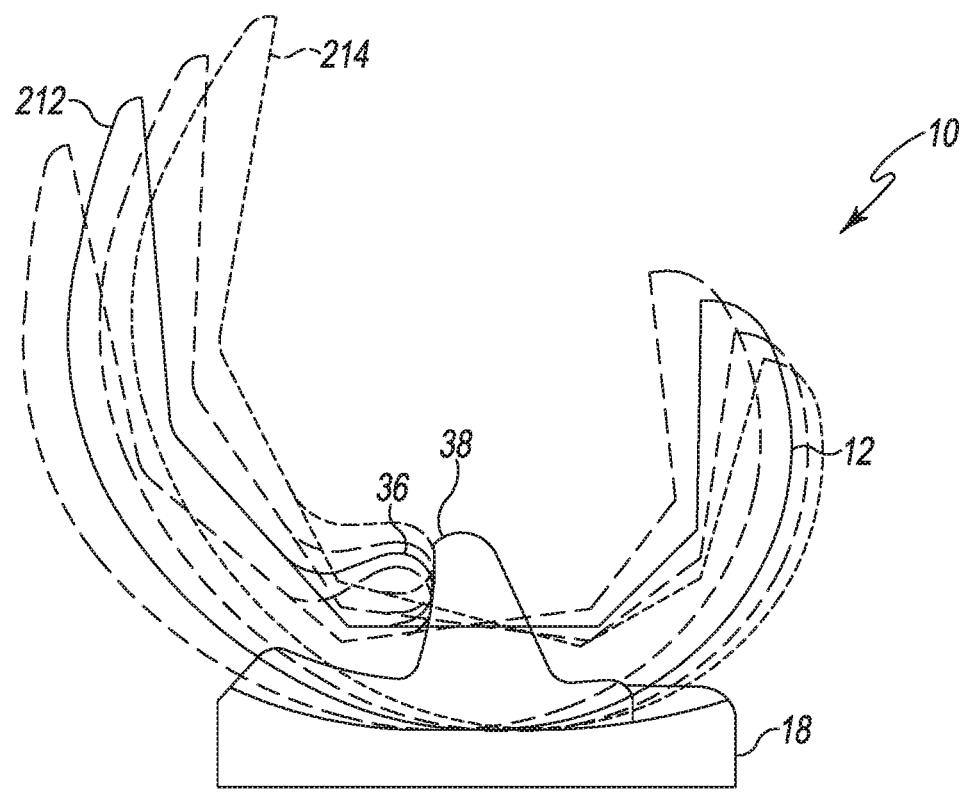
FIG. 8 is an elevation view of the replacement knee prosthesis of FIG. 1 illustrating the relative positions of the femoral component and the tibial component over a range of flexion.

Referring now to FIG. 7, the anterior wall 110 of the tibial component 14 is arcuate or rounded when the tibial component is viewed in a sagittal plane. In the illustrative embodiment, the anterior wall 100 defines a concave curved line 160 when viewed in the sagittal plane, but it should be appreciated that in other embodiments the anterior wall may define a concave curved line. In still other embodiments, the anterior wall may define a substantially straight line for a substantially flat or planar post.

The curved line 160 (and hence the anterior wall 100) has a radius 162 that extends from an origin 164. The radius 162 of the anterior wall 100 is illustratively equal to about 25 mm, but, in other embodiments, the radius 162 may be in a range of about 3 mm to about 25 mm. In still other embodiments, the radius may be greater than 25 mm. It should be appreciated that in other embodiments the radius may be greater or less than these ranges depending on the physical requirements of a particular patient.

Referring now to FIGS. 8-16, the femoral component 12 is configured to articulate on the tibial insert 18 during use. During a predetermined range of flexion, the cam 36 of the femoral component 12 contacts the post 38 of the tibial insert 18. For example, when the implant 10 is at a larger degree of flexion, the cam 36 is not in contact with the post 38. However, when the implant is at extension or is otherwise not in flexion (e.g., a flexion of about 0 degrees), the cam 36 is configured to contact the post 38 to cause axial rotation of the femoral component 12 relative to the tibial insert 18 and generally pull the femoral component 12 anteriorly.

Figure 9:
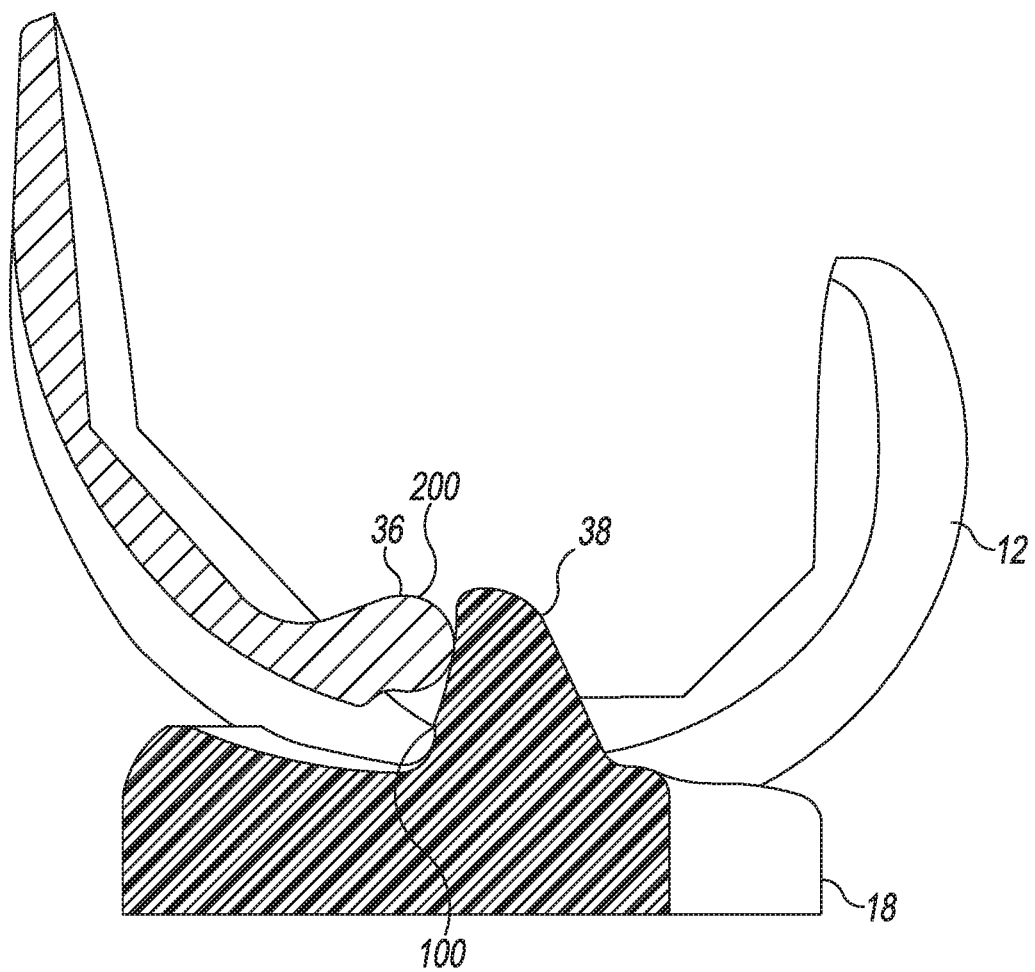
FIG. 9 is a cross-sectional elevation view illustrating the replacement knee prosthesis of FIG. 1 at about 0 degrees of flexion.
Figure 10:
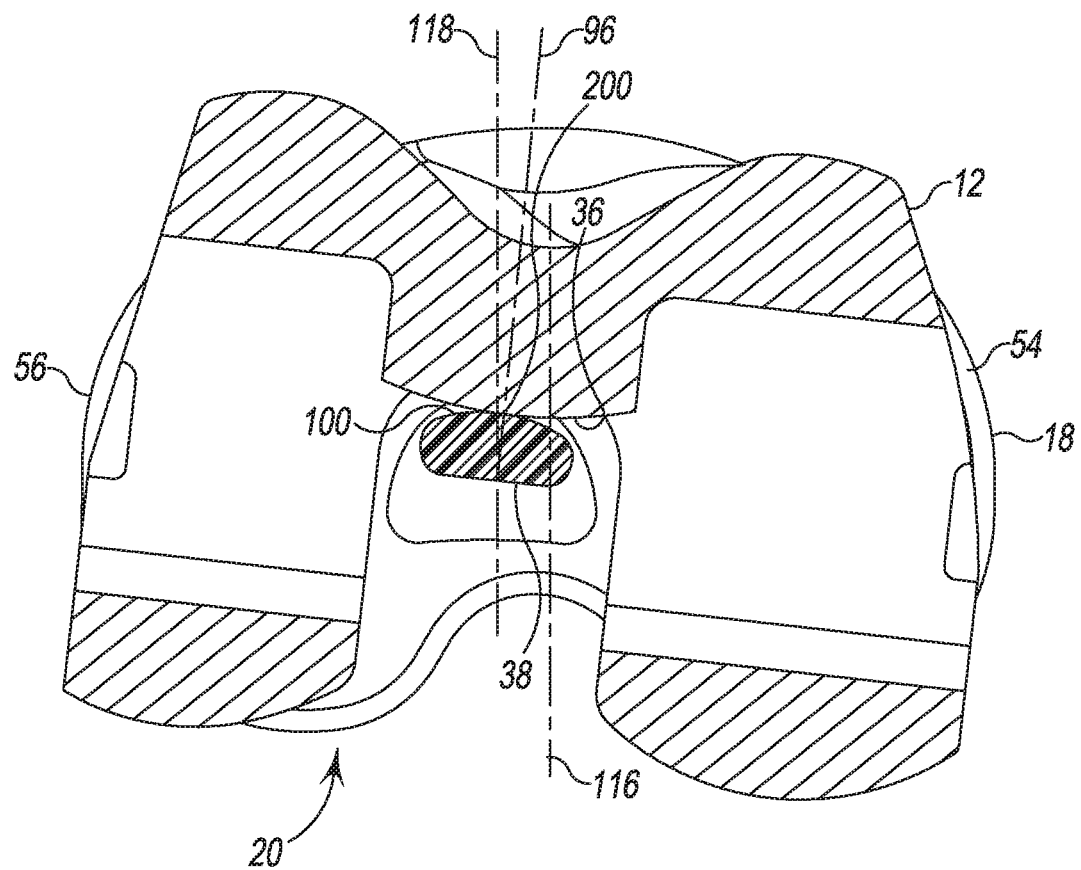
FIG. 10 is a cross-sectional plan view illustrating the replacement knee prosthesis of FIG. 9 in a plane extending perpendicular to the plane of FIG. 9 at about 0 degrees of flexion.

The anterior cam 36 of the femoral component 12 is illustrated in contact with the anterior wall 100 of the tibial post 38 at about 0 degrees of flexion in FIGS. 9-10. As shown in FIG. 10, a contact point 200 is defined at the point on the anterior wall 100 where the cam 36 engages the tibial post 38. The contact point 200 is illustratively located medial of the medial-lateral center line 118 of the post 38, and the femoral component 12 is angled on the tibial insert 18 toward the medial side of the assembly so that femoral component's center line 96 extends at an acute angle relative to the post center line 118 and the tibial insert center line 116. The tibial post 38 is offset laterally with the gap 20 of the femoral component 12.

Figure 11:
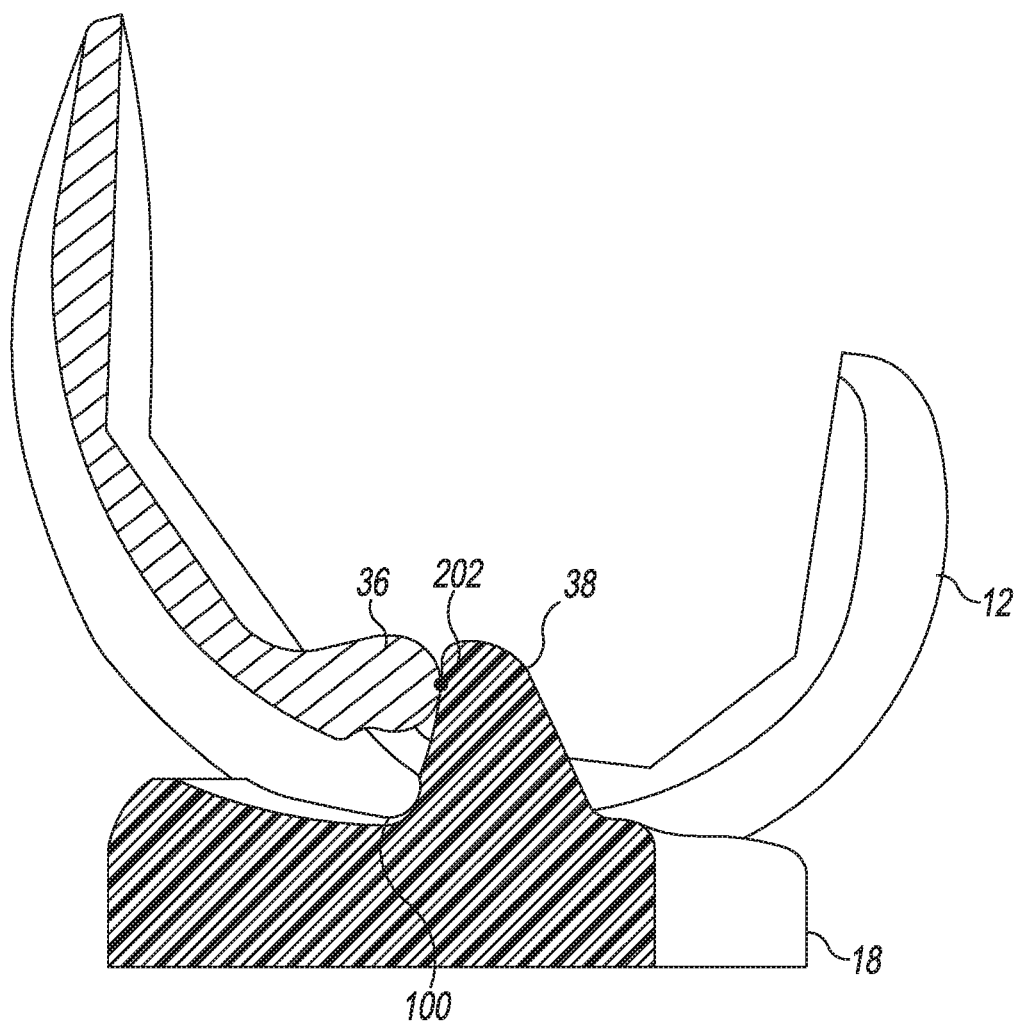
FIG. 11 is a cross-sectional elevation view similar to FIG. 9 illustrating the replacement knee prosthesis at about 7.5 degrees of flexion.
Figure 12:
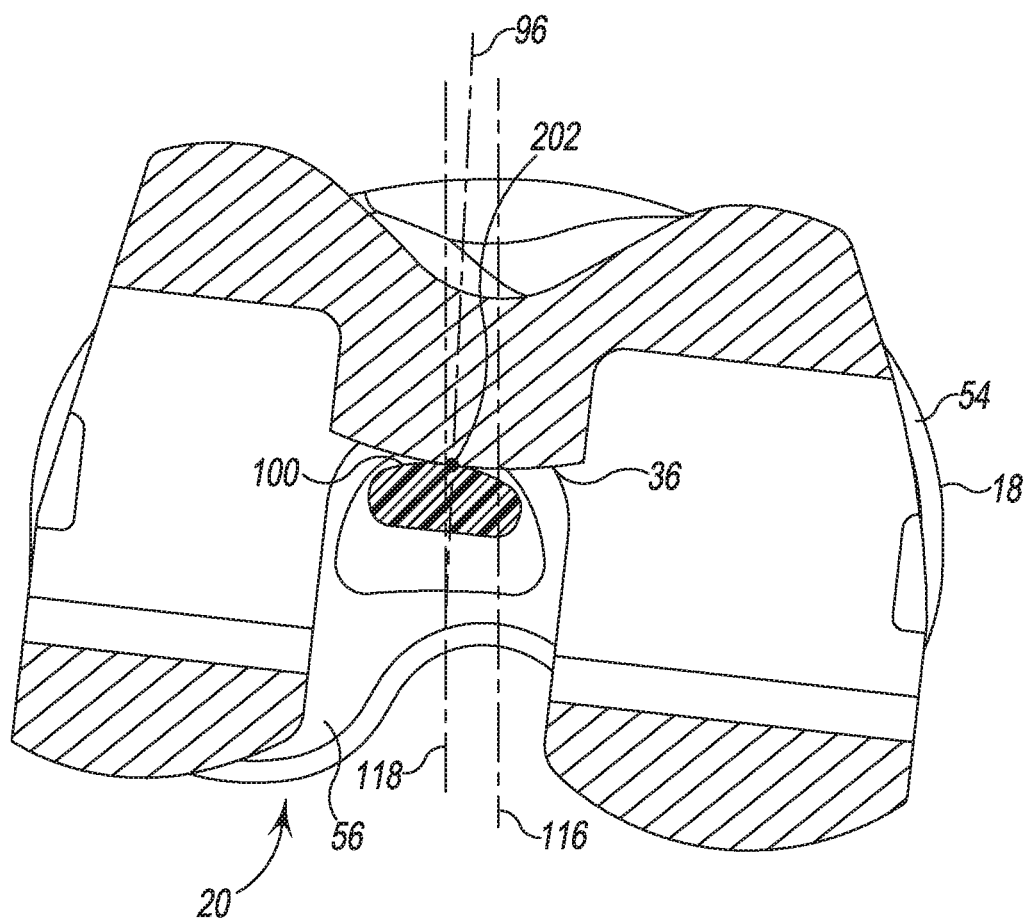
FIG. 12 is a cross-sectional plan view similar to FIG. 10 illustrating the replacement knee prosthesis at about 7.5 degrees of flexion.

As the femoral component 12 is articulated between about 0 degrees of flexion and about 7.5 degrees of flexion, the femoral component 12 rotates laterally relative to the tibial insert 18, and the contact point between the cam 36 and the post 38 moves laterally during flexion along the anterior wall 100, as shown in FIG. 12. As shown in FIG. 11, a contact point 202 is defined at the point on the anterior wall 100 where the cam 36 engages the tibial post 38. The contact point 202 is located closer to the medial-lateral center line 118 of the post 38, but the contact point 202 continues to be located medial of that line. The femoral component 12 is angled on the tibial insert 18 toward the medial side of the assembly, but a smaller angle is defined between the femoral component's center line 96 and the post center line 118 and the tibial insert center line 116. The tibial post 38 is offset laterally with the gap 20 of the femoral component 12.

Figure 13:
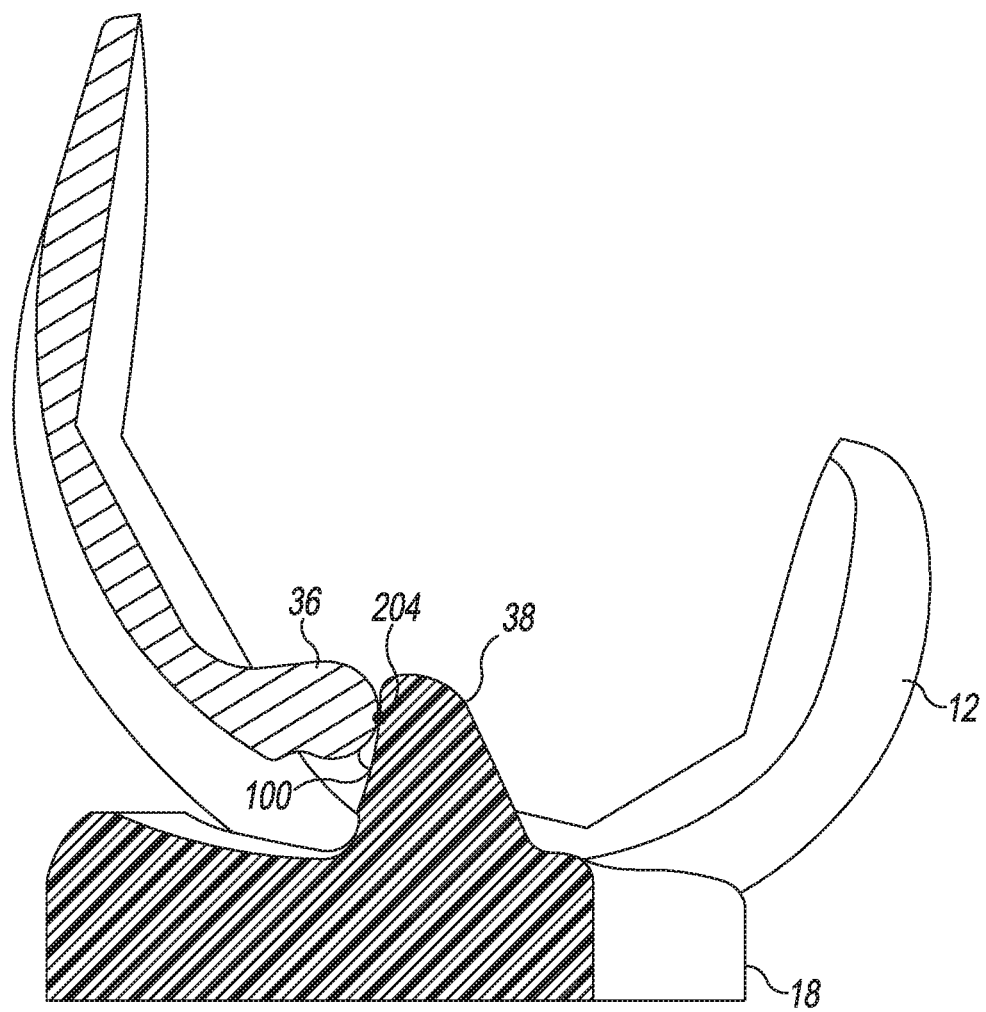
FIG. 13 is a cross-sectional elevation view similar to FIGS. 9 and 11 illustrating the replacement knee prosthesis at about 15 degrees of flexion.
Figure 14:
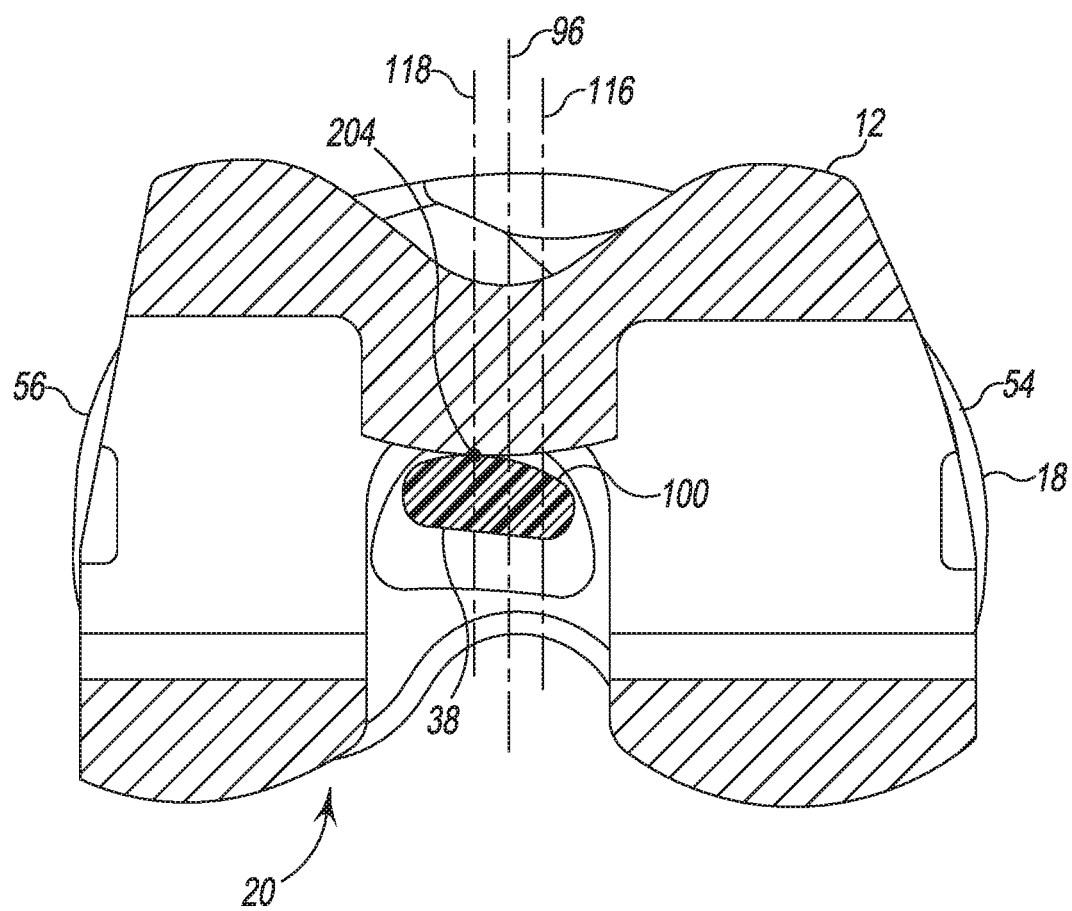
FIG. 14 is a cross-sectional plan view similar to FIGS. 10 and 12 illustrating the replacement knee prosthesis at about 15 degrees of flexion.

As the femoral component 12 is articulated between about 7.5 degrees of flexion and 15 degrees of flexion, the femoral component 12 continues to rotate laterally relative to the tibial insert 18, and the contact point between the cam 36 and the post 38 moves laterally along the anterior wall 100 during flexion, as shown in FIG. 14. As shown in FIG. 13, a contact point 204 is defined at the point on the anterior wall 100 where the cam 36 engages the tibial post 38. The contact point 204 is illustratively located approximately on the medial-lateral center line 118 of the post 38. It should be appreciated that in other embodiments the point 204 may be located lateral of the medial-lateral center line 118 of the post 38. In such embodiments, the femoral component 12 is angled on the tibial insert 18 toward the lateral side of the assembly so that femoral component's center line 96 extends at an acute angle relative to the post center line 118 and the tibial insert center line 116. In the illustrative embodiment, however, the femoral component 12 is positioned on the tibial insert 18 so that its center line 96 extends generally parallel to the tibial insert center line 116, as shown in FIG. 14. The tibial post 38 remains offset laterally with the gap 20 of the femoral component 12

Figure 15:
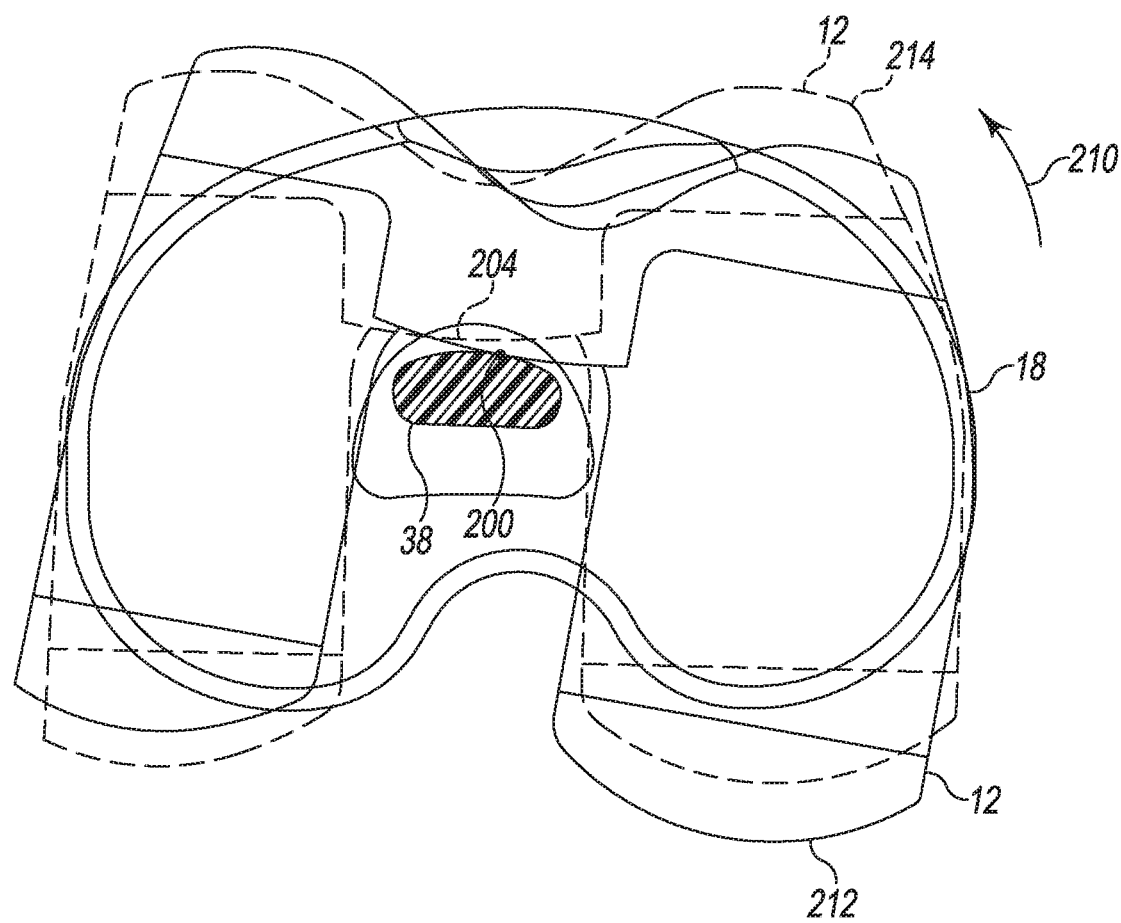
FIG. 15 is a plan view of the replacement knee prosthesis of FIG. 1 illustrating the relative positions of the femoral component and the tibial component over a range of flexion.

As described above, the femoral component 12 rotates relative to the tibial insert 18 in the direction indicated by arrow 210 in FIG. 15 as the component 12 is articulated from full extension (about 0 degrees of flexion) through about 15 degrees of flexion. In the illustrative embodiment, this rotation causes the femoral component 12 to rotate from a position 212 in which it faces toward the medial side of the assembly to a position 214 in which the femoral component 12 faces in the anterior direction. This rotation serves to reduce the inversion-eversion laxity of the patient's knee. The illustrative embodiment allows approximately 15 degrees of total rotation between about 0 degrees of flexion and about 15 degrees of flexion.

Figure 16:
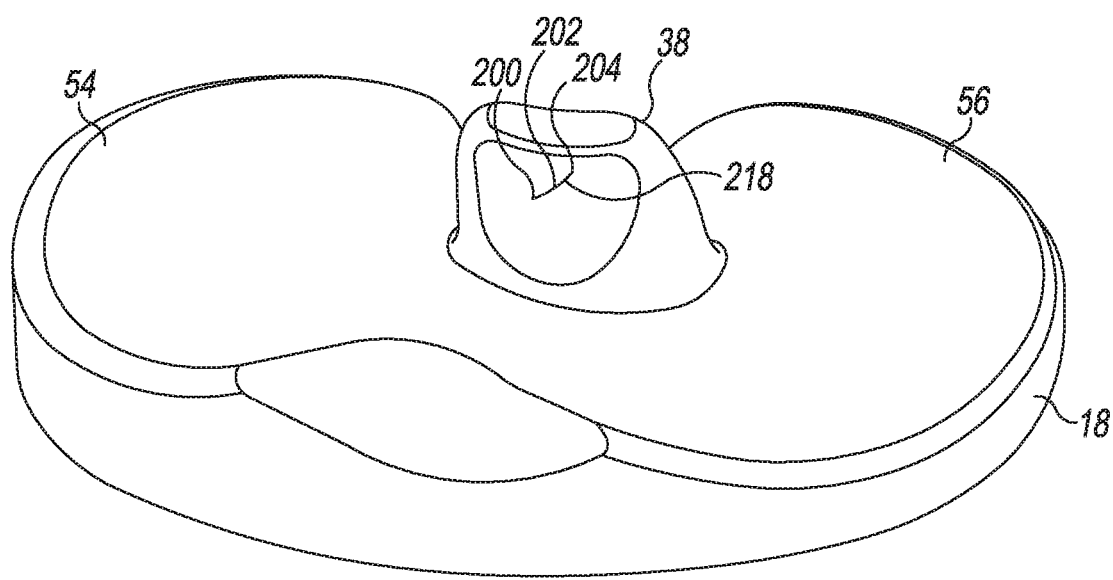
FIG. 16 is an anterior perspective view of the tibial component of the replacement knee prosthesis of FIG. 1.

As described above, the location where the cam 36 contacts the post 38 moves laterally as the femoral component 12 is articulated from about 0 degrees of flexion to about 15 degrees of flexion. As shown in FIG. 16, the contact points (including points 200, 202, 204) define an arced line 218 on the anterior wall 100 of the post 38. The cam 36 moves along the arced line 218 as the femoral component 12.

Figure 17:
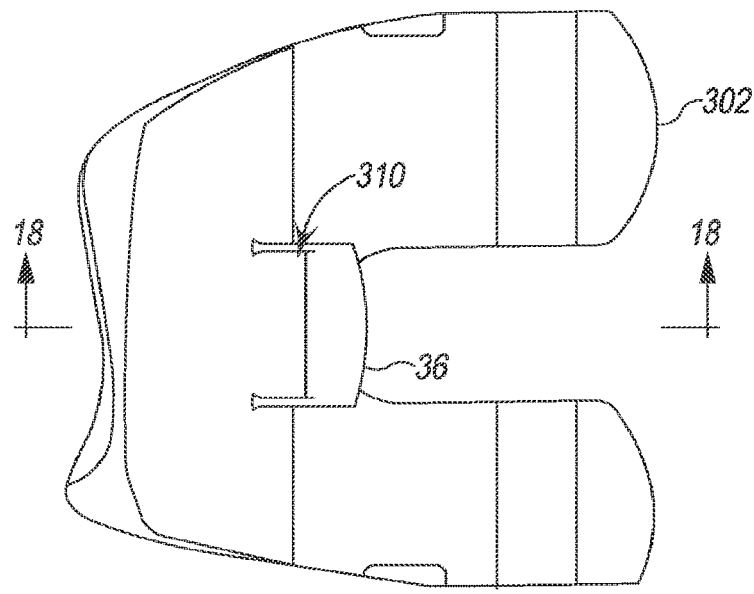
FIG. 17 is a plan view of another exemplary embodiment of a femoral component.
Figure 18:
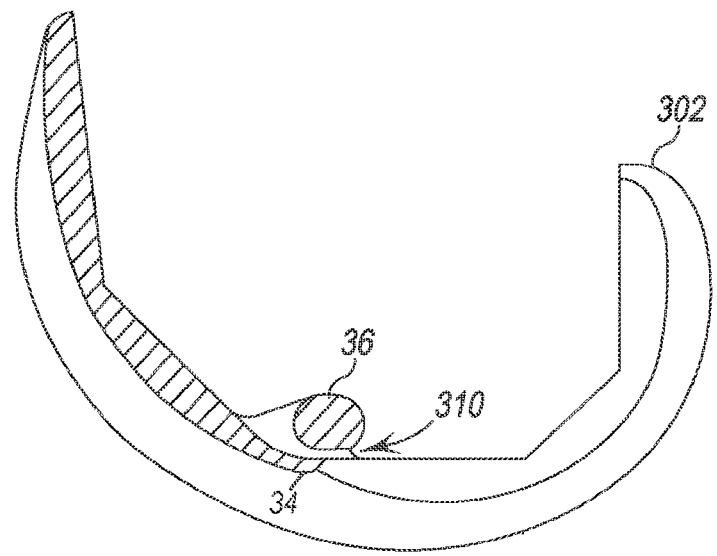
FIG. 18 is a cross-sectional elevation view taken along the line 18-18 in FIG. 17 illustrating the femoral component.

Referring now to FIGS. 17-18, another embodiment of a femoral component 302 is shown. The femoral component 302 is substantially identical to the femoral component 12 described above. Unlike the femoral component 12, the surface 64 connecting the arcuate bridge 34 and the cam 36 is omitted. As shown in FIGS. 17-18, a slot 310 is defined between the arcuate bridge 34 and the anterior cam 36 to separate those components.

As described above, the cam of the femoral component and the post of the tibial component or insert are offset in the lateral direction from the respective center lines of those components. It should be appreciated that in other embodiments, the cam of the femoral component may be centered on the center line of the femoral component with the post of the tibial component offset in the lateral direction. In such embodiments, the cam width is greater than the post width.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:

1. An orthopaedic prosthesis system, comprising:
   a femoral component configured to be coupled to a distal end of a patient's femur, the femoral component including a pair of condyles and a notch extending from an open posterior end that is defined between the pair of condyles, a tibial component configured to be coupled to a proximal end of a patient's tibia, the tibial component including an anterior edge, a posterior edge, and medial and lateral concave surfaces shaped to engage the femoral component, wherein the medial concave surface and the lateral concave surface are asymmetrical, and an anterior end of the medial concave surface is positioned superior of an anterior end of the lateral concave surface, and wherein the medial concave surface has a single distal-most point positioned a first distance from the posterior edge and a second distance from the anterior edge when the tibial component is viewed in a sagittal plane, the first distance being less than the second distance.

2. The orthopaedic prosthesis system of claim 1, wherein:
the femoral component includes a cam positioned between the pair of condyles, and
the tibial component further includes a post positioned between the medial bearing surface and the lateral bearing surface, the cam and the post being sized, shaped, and positioned so that the cam engages the post when the femoral component is in a full extension position and the cam is disengaged from the post when the femoral component is in a full flexion position.

3. The orthopaedic prosthesis system of claim 2, wherein the cam is configured to engage a contact point on the post, and the cam and the post are sized, shaped, and positioned so that the contact point moves laterally along the post when the femoral component is rotated from the full extension position toward the full flexion position.

4. The orthopaedic prosthesis system of claim 3, wherein the post has a curved anterior surface that is angled to face toward the medial bearing surface and away from the lateral bearing surface when the tibial component is viewed in a first plane positioned orthogonal to the sagittal plane, and the cam is configured to engage the curved surface at the full extension position.

5. The orthopaedic prosthesis system of claim 4, wherein the tibial component has a medial-lateral center line when the tibial component is viewed in the first plane, and the post has a medial-lateral center line that is laterally offset from the medial-lateral center line of the tibial component when the tibial component is viewed in the first plane.

6. The orthopaedic prosthesis system of claim 5, wherein the curved anterior surface of the post defines an arced line having a center point that lies on the medial-lateral center line of the post when the tibial component is viewed in the first plane.

7. The orthopaedic prosthesis system of claim 2, wherein the cam of the femoral component has a convex curved surface including a center point that is laterally offset from a center line of the femoral component when the femoral component is viewed in a first plane positioned orthogonal to the sagittal plane.

8. The orthopaedic prosthesis system of claim 2, wherein the tibial component has a medial-lateral center line when the tibial component is viewed in a first plane positioned orthogonal to the sagittal plane, and the post has a medial-lateral center line that is laterally offset from the medial-lateral center line of the tibial component when the tibial component is viewed in the first plane.

9. The orthopaedic prosthesis system of claim 8, wherein the post has an anterior surface that defines a line having a center point that lies on the medial-lateral center line of the post when the tibial component is viewed in the first plane.

10. The orthopaedic prosthesis system of claim 1, wherein the lateral bearing surface is flatter than the medial bearing surface.

11. The orthopaedic prosthesis system of claim 1, wherein the tibial component includes:
a first tibial component configured to be coupled to the proximal end of the patient's tibia, and
a second tibial component removably coupled to the first tibial component, the second tibial component including the medial bearing surface and the lateral bearing surface.

12. An orthopaedic prosthetic component, comprising:
a tibial component configured to be coupled to a proximal end of a patient's tibia, the tibial component including an anterior edge, a posterior edge, and medial and lateral concave surfaces shaped to engage a femoral component,
wherein the medial concave surface and the lateral concave surface are asymmetrical, and an anterior end of the medial concave surface is positioned superior of an anterior end of the lateral concave surface, and
wherein the medial concave surface has a single distal-most point positioned a first distance from the posterior edge and a second distance from the anterior edge when the tibial component is viewed in a sagittal plane, the first distance being less than the second distance.

13. The orthopaedic prosthetic component of claim 12, wherein the tibial component further includes a post positioned between the medial bearing surface and the lateral bearing surface, the post including an anterior surface configured to engage a cam of a femoral component when the femoral component is in a full extension position.

14. The orthopaedic prosthetic component of claim 13, wherein the anterior surface of the post is a curved anterior surface that is angled to face toward the medial bearing surface and away from the lateral bearing surface when the tibial component is viewed in a first plane positioned orthogonal to the sagittal plane.

15. The orthopaedic prosthetic component of claim 13, wherein the tibial component has a medial-lateral center line when the tibial component is viewed in a first plane positioned orthogonal to the sagittal plane, and the post has a medial-lateral center line that is laterally offset from the medial-lateral center line of the tibial component when the tibial component is viewed in the first plane.

16. The orthopaedic prosthetic component of claim 15, wherein the anterior surface of the post defines a line having a center point that lies on the medial-lateral center line of the post when the tibial component is viewed in the first plane.

17. The orthopaedic prosthesis system of claim 12, wherein the lateral bearing surface is flatter than the medial bearing surface.

18. The orthopaedic prosthesis system of claim 12, wherein the tibial component includes:
a first tibial component configured to be coupled to the proximal end of the patient's tibia, and
a second tibial component removably coupled to the first tibial component, the second tibial component including the medial bearing surface and the lateral bearing surface.

19. The orthopaedic prosthesis system of claim 1, wherein the medial concave surface and the lateral concave surface are symmetric posteriorly of the single distal-most point of the medial concave surface and asymmetric anteriorly of the single distal-most point of the medial concave surface.

20. The orthopaedic prosthetic component of claim 12, wherein the medial concave surface and the lateral concave surface are symmetric posteriorly of the single distal-most point of the medial concave surface and asymmetric anteriorly of the single distal-most point of the medial concave surface.

\* \* \* \* \*